(12) United States Patent
Mihali et al.

(10) Patent No.: US 11,635,617 B2
(45) Date of Patent: Apr. 25, 2023

(54) DIGITAL DISPLAY DEVICE COMPRISING A COMPLEMENTARY LIGHT FIELD DISPLAY OR DISPLAY PORTION, AND VISION CORRECTION SYSTEM AND METHOD USING SAME

(71) Applicant: EVOLUTION OPTIKS LIMITED, Christ Church (BB)

(72) Inventors: Raul Mihali, Westport, CT (US); Andre Michel Daniel Merizzi, Ottawa (CA); Jean-François Joly, Victoria (CA); Joseph Ivar Etigson, Toronto (CA)

(73) Assignee: EVOLUTION OPTIKS LIMITED, Bridgetown (BB)

( * ) Notice: Subject to any disclaimer, the term of this patent is extended or adjusted under 35 U.S.C. 154(b) by 38 days.

(21) Appl. No.: 17/594,662

(22) PCT Filed: Apr. 21, 2020

(86) PCT No.: PCT/US2020/029115
§ 371 (c)(1),
(2) Date: Oct. 25, 2021

(87) PCT Pub. No.: WO2020/219446
PCT Pub. Date: Oct. 29, 2020

(65) Prior Publication Data
US 2022/0197023 A1    Jun. 23, 2022

(30) Foreign Application Priority Data

Apr. 23, 2019  (CA) .............................. CA 3040952
Jun. 5, 2019   (CA) .............................. CA 3045261

(51) Int. Cl.
*G09G 5/00*     (2006.01)
*G02B 27/00*    (2006.01)
(Continued)

(52) U.S. Cl.
CPC ....... *G02B 27/0093* (2013.01); *G02B 3/0037* (2013.01); *G02B 30/26* (2020.01);
(Continued)

(58) Field of Classification Search
CPC ....... A61B 3/0041; A61B 3/028; A61B 3/113; B60K 2370/20; B60K 2370/741;
(Continued)

(56) References Cited

U.S. PATENT DOCUMENTS 5,032,754 A    7/1991  Iwao et al.
5,959,664 A    9/1999  Woodgate
(Continued)

FOREIGN PATENT DOCUMENTS

AU    2015100739       7/2015
DE    9410161 U1      12/1994
(Continued)

OTHER PUBLICATIONS

U.S. Appl. No. 17/302,392, filed Apr. 30, 2021, Guillaume Lussier, Entire Document.
(Continued)

*Primary Examiner* — Insa Sadio
(74) *Attorney, Agent, or Firm* — Knobbe, Martens, Olson & Bear, LLP

(57) ABSTRACT

Described are various embodiments of a digital display device to render an image for viewing by a viewer having reduced visual acuity, the device comprising: a digital display medium for rendering the image based on pixel data related thereto; a complementary light field display portion; and a hardware processor operable on said pixel data for a selected portion of the image to be rendered via said complementary light field display portion so to produce vision-corrected pixel data corresponding thereto to at least partially address the viewer's reduced visual acuity when
(Continued)

viewing said selected portion as rendered in accordance with said vision-corrected pixel data by said complementary light field display portion.

20 Claims, 14 Drawing Sheets

(51) Int. Cl.
  *G02B 30/26* (2020.01)
  *G02B 3/00* (2006.01)
  *G06F 1/16* (2006.01)
  *G06F 3/01* (2006.01)
  *G06F 3/03* (2006.01)
(52) U.S. Cl.
  CPC ............ *G06F 1/165* (2013.01); *G06F 1/1626* (2013.01); *G06F 1/1686* (2013.01); *G06F 3/013* (2013.01); *G06F 3/0304* (2013.01)
(58) Field of Classification Search
  CPC ....... B60K 35/00; G06F 1/1626; G06F 1/165; G06F 1/1686; G06F 3/013; G06F 3/0304; G02B 2027/0138; G02B 2027/014; G02B 23/12; G02B 27/0093; G02B 3/0037; G02B 30/26; G02B 30/27; G09B 21/008; G09G 2354/00; G09G 5/00
  See application file for complete search history.

(56) References Cited

U.S. PATENT DOCUMENTS

| | | |
|---|---|---|
| 6,192,341 B1 | 2/2001 | Becker et al. |
| 6,309,117 B1 | 10/2001 | Bunce et al. |
| 6,386,707 B1 | 5/2002 | Pellicano |
| 6,417,867 B1 | 7/2002 | Hallberg |
| 6,483,485 B1 | 11/2002 | Huang et al. |
| 6,536,907 B1 | 3/2003 | Towner et al. |
| 6,543,898 B1 | 4/2003 | Griffin et al. |
| 6,784,905 B2 | 8/2004 | Brown et al. |
| 6,809,704 B2 | 10/2004 | Kulas |
| 6,820,979 B1 | 11/2004 | Stark et al. |
| 6,876,758 B1 | 4/2005 | Polat et al. |
| 6,953,249 B1 | 10/2005 | Maguire, Jr. |
| 7,062,547 B2 | 6/2006 | Brown et al. |
| 7,147,605 B2 | 12/2006 | Ragauskas |
| 7,517,086 B1 | 4/2009 | Kürkure |
| 7,819,818 B2 | 10/2010 | Ghajar |
| 7,866,817 B2 | 1/2011 | Polat |
| 7,891,813 B2 | 2/2011 | Ogilvie |
| 7,973,850 B2 | 7/2011 | Ishiga |
| 8,089,512 B2 | 1/2012 | Okabe et al. |
| 8,098,440 B2 | 1/2012 | Jethmalani et al. |
| 8,164,598 B2 | 4/2012 | Kimpe |
| 8,231,220 B2 | 7/2012 | Baranton |
| 8,322,857 B2 | 12/2012 | Barbur et al. |
| 8,540,375 B2 | 9/2013 | Destain |
| 8,717,254 B1 | 5/2014 | Nave et al. |
| 8,783,871 B2 | 7/2014 | Pamplona et al. |
| 8,798,317 B2 | 8/2014 | Wu |
| 8,823,742 B2 | 9/2014 | Kweon |
| 8,857,984 B2 | 10/2014 | Clarke et al. |
| 8,967,809 B2 | 3/2015 | Kirschen et al. |
| 9,010,929 B2 | 4/2015 | Lewis |
| 9,041,833 B2 | 5/2015 | Hatakeyama |
| 9,052,502 B2 | 6/2015 | Caldeira et al. |
| 9,066,683 B2 | 6/2015 | Zhou |
| 9,104,233 B2 | 8/2015 | Alberth |
| 9,159,299 B2 | 10/2015 | Lee |
| 9,177,355 B1 | 11/2015 | Buchheit |
| 9,183,806 B2 | 11/2015 | Felt |
| 9,198,571 B2 | 12/2015 | Kiderman et al. |
| 9,301,680 B2 | 4/2016 | Fassi et al. |
| 9,307,940 B2 | 4/2016 | MacLullich et al. |
| 9,492,074 B1 | 11/2016 | Lee et al. |
| 9,642,522 B2 | 5/2017 | Samadani et al. |
| 9,844,323 B2 | 12/2017 | Pamplona et al. |
| 9,895,057 B2 | 2/2018 | Tumlinson |
| 10,058,241 B2 | 8/2018 | Patella et al. |
| 10,085,631 B2 | 10/2018 | Shimizu et al. |
| 10,182,717 B2 | 1/2019 | Lindig et al. |
| 10,206,566 B2 | 2/2019 | Skolianos et al. |
| 10,247,941 B2 | 4/2019 | Fürsich |
| 10,335,027 B2 | 7/2019 | Pamplona et al. |
| 10,345,590 B2 | 7/2019 | Samec et al. |
| 10,394,322 B1 | 8/2019 | Gotsch |
| 10,420,467 B2 | 9/2019 | Krall et al. |
| 10,548,473 B2 | 2/2020 | Escalier et al. |
| 10,761,604 B2 | 9/2020 | Gotsch et al. |
| 2002/0024633 A1 | 2/2002 | Kim et al. |
| 2002/0099305 A1 | 7/2002 | Fukushima et al. |
| 2004/0119714 A1 | 6/2004 | Everett et al. |
| 2006/0119705 A1 | 6/2006 | Liao |
| 2008/0129957 A1 | 6/2008 | Mellon et al. |
| 2008/0309764 A1 | 12/2008 | Kubota et al. |
| 2009/0290132 A1 | 11/2009 | Shevlin |
| 2010/0156214 A1 | 6/2010 | Yang |
| 2010/0277693 A1 | 11/2010 | Martinez-Conde et al. |
| 2010/0298735 A1 | 11/2010 | Suffin |
| 2011/0019056 A1 | 1/2011 | Hirsch et al. |
| 2011/0122144 A1 | 5/2011 | Gabay |
| 2011/0157180 A1 | 6/2011 | Burger et al. |
| 2011/0268868 A1 | 11/2011 | Dowski, Jr. et al. |
| 2012/0010474 A1 | 1/2012 | Olsen et al. |
| 2012/0113389 A1 | 5/2012 | Mukai et al. |
| 2012/0206445 A1 | 8/2012 | Chiba |
| 2012/0249951 A1 | 10/2012 | Hirayama |
| 2012/0254779 A1 | 10/2012 | Ollivierre et al. |
| 2012/0262477 A1 | 10/2012 | Buchheit |
| 2013/0027384 A1 | 1/2013 | Ferris |
| 2013/0096820 A1 | 4/2013 | Agnew |
| 2013/0120390 A1 | 5/2013 | Marchand et al. |
| 2013/0222652 A1 | 8/2013 | Akeley et al. |
| 2014/0028662 A1 | 1/2014 | Liao et al. |
| 2014/0055692 A1 | 2/2014 | Kroll et al. |
| 2014/0063332 A1 | 3/2014 | Miyawaki |
| 2014/0118354 A1 | 5/2014 | Pais et al. |
| 2014/0137054 A1 | 5/2014 | Gandhi et al. |
| 2014/0200079 A1 | 7/2014 | Bathiche et al. |
| 2014/0253876 A1 | 9/2014 | Klin et al. |
| 2014/0267284 A1 | 9/2014 | Blanche et al. |
| 2014/0268060 A1 | 9/2014 | Lee et al. |
| 2014/0282285 A1 | 9/2014 | Sadhvani et al. |
| 2014/0327750 A1 | 11/2014 | Malachowsky et al. |
| 2014/0327771 A1 | 11/2014 | Malachowsky et al. |
| 2014/0340390 A1 | 11/2014 | Lanman et al. |
| 2015/0049390 A1 | 2/2015 | Lanman et al. |
| 2015/0177514 A1 | 6/2015 | Maimone et al. |
| 2015/0185501 A1* | 7/2015 | Bakaraju ............... A61F 2/1451 351/159.79 |
| 2015/0234187 A1 | 8/2015 | Lee |
| 2015/0234188 A1 | 8/2015 | Lee |
| 2015/0262424 A1 | 9/2015 | Tabaka et al. |
| 2015/0336511 A1 | 11/2015 | Ukeda |
| 2016/0042501 A1 | 2/2016 | Huang et al. |
| 2016/0103419 A1 | 4/2016 | Callagy et al. |
| 2016/0134815 A1 | 5/2016 | Ishiguro et al. |
| 2016/0306390 A1 | 10/2016 | Vertegaal et al. |
| 2016/0335749 A1 | 11/2016 | Kano |
| 2017/0027435 A1 | 2/2017 | Boutinon et al. |
| 2017/0060399 A1 | 3/2017 | Hough et al. |
| 2017/0212352 A1 | 7/2017 | Cobb et al. |
| 2017/0227781 A1* | 8/2017 | Banerjee ................ G02B 27/14 |
| 2017/0302913 A1 | 10/2017 | Tonar et al. |
| 2017/0307898 A1 | 10/2017 | Vdovin et al. |
| 2017/0353717 A1 | 12/2017 | Zhou et al. |
| 2017/0365101 A1 | 12/2017 | Samec et al. |
| 2017/0365189 A1 | 12/2017 | Halpin et al. |
| 2018/0070820 A1 | 3/2018 | Fried et al. |
| 2018/0084245 A1 | 3/2018 | Lapstun |
| 2018/0136486 A1 | 5/2018 | Macnamara et al. |
| 2018/0203232 A1 | 7/2018 | Bouchier et al. |
| 2018/0252935 A1 | 9/2018 | Vertegaal et al. |

(56) References Cited

U.S. PATENT DOCUMENTS

| | | | |
|---|---|---|---|
| 2018/0290593 | A1 | 10/2018 | Cho |
| 2018/0330652 | A1 | 11/2018 | Perreault et al. |
| 2019/0125179 | A1 | 5/2019 | Xu et al. |
| 2019/0150729 | A1 | 5/2019 | Huang et al. |
| 2019/0175011 | A1 | 6/2019 | Jensen et al. |
| 2019/0228586 | A1 | 7/2019 | Bar-Zeev et al. |
| 2019/0246095 | A1 | 8/2019 | Kishimoto |
| 2019/0246889 | A1 | 8/2019 | Marin et al. |
| 2019/0310478 | A1 | 10/2019 | Marin et al. |
| 2020/0012090 | A1 | 1/2020 | Lapstun |

FOREIGN PATENT DOCUMENTS

| | | | |
|---|---|---|---|
| DE | 102004038822 | A1 | 3/2006 |
| DE | 102016212761 | | 5/2018 |
| DE | 102018121742 | A1 | 3/2020 |
| DE | 102018129600 | A1 | 5/2020 |
| DE | 102019102373 | A1 | 7/2020 |
| EP | 2127949 | A1 | 12/2009 |
| EP | 1509121 | B1 | 9/2012 |
| EP | 2589020 | A2 | 5/2013 |
| EP | 2678804 | A1 | 1/2014 |
| EP | 2760329 | A1 | 8/2014 |
| EP | 2999393 | A1 | 3/2016 |
| EP | 2547248 | B1 | 5/2017 |
| EP | 3262617 | A1 | 1/2018 |
| EP | 3339943 | A1 | 6/2018 |
| EP | 3367307 | A3 | 12/2018 |
| EP | 2828834 | B1 | 11/2019 |
| EP | 3620846 | A1 | 3/2020 |
| EP | 3631770 | A1 | 4/2020 |
| EP | 3657440 | A1 | 5/2020 |
| EP | 3659109 | A1 | 6/2020 |
| EP | 3689225 | A1 | 8/2020 |
| EP | 3479344 | B1 | 12/2020 |
| FR | 3059537 | B1 | 5/2019 |
| JP | 2003038443 | A | 2/2003 |
| WO | 2011156721 | A1 | 12/2011 |
| WO | 2013166570 | A1 | 11/2013 |
| WO | 2014174168 | A1 | 10/2014 |
| WO | 2014197338 | A2 | 12/2014 |
| WO | 2015162098 | A1 | 10/2015 |
| WO | 2017192887 | A2 | 11/2017 |
| WO | 2017218539 | A1 | 12/2017 |
| WO | 2018022521 | A1 | 2/2018 |
| WO | 2018092989 | A1 | 5/2018 |
| WO | 2018129310 | A1 | 7/2018 |
| WO | WO2021038421 | A1 | 8/2020 |
| WO | WO2021087384 | | 10/2020 |
| WO | 2021122640 | A1 | 6/2021 |

OTHER PUBLICATIONS

U.S. Appl. No. 17/309,133, filed Apr. 29, 2021, Daniel Gotsch, Entire Document.

"A Computational Light Field Display for Correcting Visual Aberrations," Huang, F.C., Technical Report No. UCB/EECS-2013-206, Electrical Engineering and Computer Sciences University of California at Berkeley, http://www.eecs.berkeley.edu/Pubs/TechRpts/2013/EECS-2013-206.html, Dec. 15, 2013.

"Eyeglasses-free Display: Towards Correcting Visual Aberrations with Computational Light Field Displays", by Huang at al., taken from http://web.media.mit.edu/~gordonw/VisionCorrectingDisplay/, published Aug. 2, 2014, pp. 1-15.

Agus M. et al., "GPU Accelerated Direct Volume Rendering on an Interactive Light Field Display", Eurographics 2008, vol. 27, No. 2, 2008.

Burnett T., "FoVI3D Extreme Multi-view Rendering for Light-field Displays", GTC 2018 (GPU Technology Conference), Silicon Valley, 2018.

Ciuffreda, Kenneth J., et al., Understanding the effects of mild traumatic brain injury on the pupillary light reflex, Concussion (2017) 2(3), CNC36.

Fattal, D. et al., A Multi-Directional Backlight for a Wide-Angle, Glasses-Free Three-Dimensional Display, Nature, Mar. 21, 2013, pp. 348-351, vol. 495.

Fielmann Annual Report 2019 (https://www.fielmann.eu/downloads/fielmann_annual_report_2019.pdf).

Gray, Margot, et al., Female adolescents demonstrate greater oculomotor and vestibular dysfunction than male adolescents following concussion, Physical Therapy in Sport 43 (2020) 68-74.

Halle M., "Autostereoscopic displays and computer graphics", Computer Graphics, ACM SIGGRAPH, 31(2), May 1997, pp. 58-62.

Howell, David R., et al., Near Point of Convergence and Gait Deficits in Adolescents After Sport-Related Concussion, Clin J Sport Med, 2017.

Howell, David R., et al., Receded Near Point of Convergence and Gait are Associated After Concussion, Br J Sports Med, Jun. 2017; 51:e1, p. 9 (Abstract).

Huang, F.C. et al., "Eyeglasses-Free Display: Towards Correcting Visual Aberrations With Computational Light Field Displays,", ACM Transactions on Graphics (TOG)—Proceedings of ACM SIGGRAPH 2014, vol. 33, Issue 4, Article No. 59 , Jul. 2014.

Kawata, K., et al., Effect of Repetitive Sub-concussive Head Impacts on Ocular Near Point of Convergence, In t. J Sports Med 2016; 37; 405-410.

Lewin, Sarah "No Need for Reading Glasses With Vision-Correcting Display", published 2014.

Mainone, Andrew, et al. "Focus 3D: Compressive accommodation display." ACM Trans. Graph. 32.5 (2013): 153-1.

Masia B. et al., "A survey on computational displays: Pushing the boundaries of optics, computation, and perception", Computer & Graphics, vol. 37, 2013, pp. 1012-1038.

Murray, Nicholas G., et al., Smooth Pursuit and Saccades after Sport-Related Concussion, Journal of Neurotrauma 36: 1-7 (2019).

Pamplona V. F. et al., "Tailored Displays to Compensate for Visual Aberrations," ACM Transactions on Graphics (TOG), Jul. 2012 Article No. 81, https://doi.org/10.1145/2185520.2185577.

Pamplona V. F., Thesis (PhD.)—Universidade Federal do Rio Grande do Sul. Programa de Pós-Graduação em Computação, Porto Alegre, BR-RS, 2012. Advisor: Manuel Menezes de Oliveira Neto.

Ventura, Rachel E., et al., Diagnostic Tests for Concussion: Is Vision Part of the Puzzle?, Journal of Neuro-Ophthalmology 2015; 35; 73-81.

Wetzstein, G. et al., "Tensor Displays: Compressive Light Field Synthesis using Multilayer Displays with Directional Backlighting", https://web.media.mit.edu/~gordonw/TensorDisplays/TensorDisplays.pdf.

Zahid, Abdullah Bin, et al., Eye Tracking as a Biomarker for Concussion in Children, Clin J Sport Med 2018.

* cited by examiner

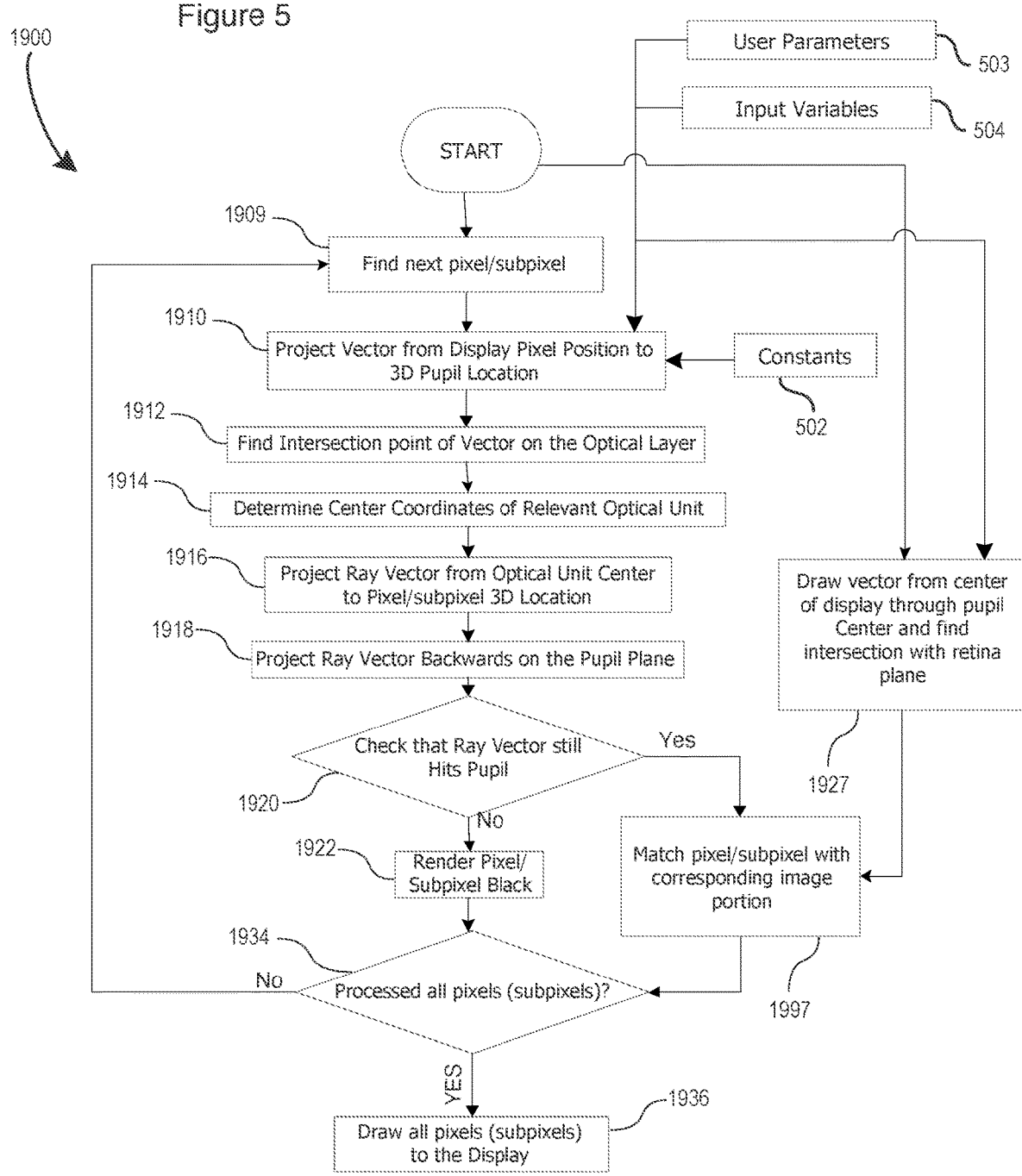

DIGITAL DISPLAY DEVICE COMPRISING A COMPLEMENTARY LIGHT FIELD DISPLAY OR DISPLAY PORTION, AND VISION CORRECTION SYSTEM AND METHOD USING SAME

CROSS REFERENCE TO RELATED APPLICATIONS

This application the U.S. National Phase Application under 35 U.S.C. § 371 of International Application No. PCT/US2020/029115, filed Apr. 21, 2020, which claims priority to Canadian Patent Application No. 3,040,952 filed Apr. 23, 2019 and Canadian Patent Application No. 3,045,261 filed Jun. 5, 2019, the entire disclosure of each of which is hereby incorporated herein by reference.

FIELD OF THE DISCLOSURE

The present disclosure relates to digital display devices and systems, and in particular, to a digital display device comprising a complementary light filed display portion, and vision correction system and method user same.

BACKGROUND

Individuals routinely wear corrective lenses to accommodate for reduced vision acuity in consuming images and/or information rendered, for example, on digital displays provided, for example, in day-to-day electronic devices such as smartphones, smart watches, electronic readers, tablets, laptop computers and the like, but also provided as part of vehicular dashboard displays and entertainment systems, to name a few examples. The use of bifocals or progressive corrective lenses is also commonplace for individuals suffering from near and far sightedness.

The operating systems of current electronic devices having graphical displays offer certain "Accessibility" features built into the software of the device to attempt to provide users with reduced vision the ability to read and view content on the electronic device. Specifically, current accessibility options include the ability to invert images, increase the image size, adjust brightness and contrast settings, bold text, view the device display only in grey, and for those with legal blindness, the use of speech technology. These techniques focus on the limited ability of software to manipulate display images through conventional image manipulation, with limited success.

Light field displays using lenslet arrays or parallax barriers have been proposed for correcting such visual aberrations. For a thorough review of Autostereoscopic or light field displays, Halle M. (Halle, M., "Autostereoscopic displays and computer graphics" ACM SIGGRAPH, 31(2), pp. 58-62, 1997) gives an overview of the various ways to build a glasses-free 3D display, including but not limited to parallax barriers, lenticular sheets, microlens arrays, holograms, and volumetric displays for example. Moreover, the reader is also directed to another article by Masia et al. (Masia B., Wetzstein G., Didyk P. and Gutierrez, "A survey on computational displays: Pushing the boundaries of optics, computation and perception", Computer & Graphics 37 (2013), 1012-1038) which also provides a good review of computational displays, notably light field displays at section 7.2 and vision correcting light field displays at section 7.4.

An example of using light field displays to correct visual aberrations has been proposed by Pamplona et al. (PAMPLONA, V., OLIVEIRA, M., ALIAGA, D., AND RASKAR, R. 2012. "Tailored displays to compensate for visual aberrations." ACM Trans. Graph. (SIGGRAPH) 31.). Unfortunately, conventional light field displays as used by Pamplona et al. are subject to a spatio-angular resolution trade-off; that is, an increased angular resolution decreases the spatial resolution. Hence, the viewer sees a sharp image but at the expense of a significantly lower resolution than that of the screen. To mitigate this effect, Huang et al. (see, HUANG, F.-C., AND BARSKY, B. 2011. A framework for aberration compensated displays. Tech. Rep. UCB/EECS-2011-162, University of California, Berkeley, December; and HUANG, F.-C., LANMAN, D., BARSKY, B. A., AND RASKAR, R. 2012. Correcting for optical aberrations using multi layer displays. ACM Trans. Graph. (SiGGRAPH Asia) 31, 6, 185:1-185:12, proposed the use of multilayer display designs together with prefiltering. The combination of prefiltering and these particular optical setups, however, significantly reduces the contrast of the resulting image.

Moreover, in U.S. Patent Application Publication No. 2016/0042501 and Fu-Chung Huang, Gordon Wetzstein, Brian A. Barsky, and Ramesh Raskar. "Eyeglasses-free Display: Towards Correcting Visual Aberrations with Computational Light Field Displays". *ACM Transaction on Graphics*, xx:0, August 2014, the entire contents of each of which are hereby incorporated herein by reference, the combination of viewer-adaptive pre-filtering with off-the-shelf parallax barriers has been proposed to increase contrast and resolution, at the expense however, of computation time and power.

Another example includes the display of Wetzstein et al. (Wetzstein, G. et al., "Tensor Displays: Compressive Light Field Synthesis using Multilayer Displays with Directional Backlighting", https://web.media.mit.edu/~gordonw/TensorDisplays/Tensor Displays.pdf) which disclose a glass-free 3D display comprising a stack of time-multiplexed, light-attenuating layers illuminated by uniform or directional backlighting. However, the layered architecture may cause a range of artefacts including Moiré effects, color-channel crosstalk, interreflections, and dimming due to the layered color filter array. Similarly, Agus et al. (AGUS M. et al., "GPU Accelerated Direct Volume Rendering on an Interactive Light Field Display", EUROGRAPHICS 2008, Volume 27, Number 2, 2008) disclose a GPU accelerated volume ray casting system interactively driving a multi-user light field display. The display, produced by the Holographika company, uses an array of specially arranged array of projectors and a holographic screen to provide glass-free 3D images. However, the display only provides a parallax effect in the horizontal orientation as having parallax in both vertical and horizontal orientations would be too computationally intensive. Finally, the FOVI3D company (http://on-demand.gputechconf.com/gtc/2018/presentation/s8461-extreme-multi-view-rendering-for-light-field-displays.pdf) provides light field displays wherein the rendering pipeline is a replacement for OpenGL which transports a section of the 3D geometry for further processing within the display itself. This extra processing is possible because the display is integrated into a bulky table-like device.

While the above-noted references propose some light field display solutions, most suffer from one or more drawbacks which limits their commercial viability, particularly in seeking to provide vision correction solutions, but also in providing other image perception adjustments and experiences.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for a digital display device and solution that overcome some of the drawbacks of known techniques, or at least, provide a useful alternative thereto. Some aspects of the disclosure provide embodiments of such devices and solutions, such as a digital display device comprising a complementary light filed display operatively coupled thereto, and vision correction system and method user same.

In accordance with one aspect, there is provided a selective light field display device operable to provide selective vision correction or display perceptions for at least one portion or region of the display, or for at least one display image feature thereof. For example, one such portion may comprise a text region to be displayed via the light field display such that image corrected text, or the text font displayed as part thereof, can be more readily perceived by a viewer having reduced visual acuity. Namely, vision correction applications as described herein may be implemented for the purposes of adjusting a perception of a selected image portion to be rendered on a digital display screen, or text thereof, by associating adjusted or vision corrected pixel data with display pixels that, when rendered and projected through a light field shaping layer (LFSL), results in an adjusted perception of the selected image portion or text thereof.

In some embodiments, a digitally executed ray tracing process can be implemented to effectively shape the light field emanating from the light field display in respect of the selected display region or text of interest so to accommodate for the viewer's reduced visual acuity and thereby improve a perception of these selected regions by the user. In doing so, only image pixels associated with the region(s) of interest need be processed by the vision correction application to apply the desired image perception adjustment thereto, for instance resulting in sharper and more discernable features (e.g. text, lines, image detail) in the selected region(s).

In some embodiments in which portions of interest comprises text portions, vision corrected font patterns may result from such a ray tracing process, and/or again, may be retrieved from a shared, local, remote or temporarily stored digital library of such vision corrected font patterns, to produce the vision corrected text.

In accordance with one aspect, there is provided a digital display device to render text for viewing by a viewer having reduced visual acuity, the device comprising: a digital display medium comprising an array of pixels; a light field shaping layer (LFSL) defined by an array of LFSL elements and disposed relative to said digital display medium so to dispose each of said LFSL elements over an underlying set of said pixels to shape a light field emanating therefrom and thereby at least partially govern a projection thereof from said display medium toward the viewer; and a hardware processor operable on pixel data to output corrective font pixel data to be rendered via said digital display medium and projected through said LFSL so to produce vision-corrected text to at least partially address the viewer's reduced visual acuity when viewing the text.

In one embodiment, the corrective font pixel data for distinct text characters in the text corresponds to distinct corrective light field font pixel patterns that, when projected through said LFSL, render distinct vision corrected text characters accordingly.

In one embodiment, each of said distinct corrective light field font pixel patterns in the text is stored and retrieved from a digital corrective font pattern library.

In one embodiment, the distinct corrective light field font pixel patterns are stored as a function of a corrective power defined at least in part by the viewer's reduced visual acuity.

In one embodiment, pixel data associated with background pixels outside an area of said distinct corrective light filed font pixel patterns are is adjusted so to increase a background contrast with vision-corrected text.

In accordance with another aspect, there is provided a method, to be implemented by a digital data processor, to render text for viewing by a viewer having reduced visual acuity via a digital display medium comprising an array of pixels and having a light field shaping layer (LFSL) defined therefor, the method comprising: identifying a text area to be correctively rendered; defining corrective font pixel data to be rendered via the digital display medium and projected through the LFSL so to produce vision-corrected text; and rendering the corrective font pixel data so to produce said vision-corrected text to at least partially address the viewer's reduced visual acuity.

In one embodiment, the defining comprises defining said corrective font pixel data for distinct text characters in the text to correspond to distinct corrective light field font pixel patterns that, when projected through said LFSL, render distinct vision corrected text characters accordingly.

In one embodiment, the identifying comprises automatically recognizing said distinct text characters, and wherein said defining comprises retrieving from digital storage said distinct corrective light field font pixel patterns corresponding to said automatically recognized text characters.

In one embodiment, the defining comprises executing a digitally implemented ray-tracing process to: digitally map the text on an adjusted image plane designated to at least partially address the viewer's reduced visual acuity; and associate said corrective font pixel data with corresponding pixels according to said mapping and a physical geometry of the display medium and the viewer.

In one embodiment, the adjusted image plane is a virtual image plane virtually positioned relative to the digital display at a designated distance from the viewer.

In one embodiment, the designated distance comprises a minimum viewing distance designated a function of the viewer's reduced visual acuity.

In one embodiment, the adjusted image plane is designated as a user retinal plane.

In accordance with another aspect, there is provided a digital display device to render an input image for viewing by a viewer having reduced visual acuity, the device comprising: a digital display medium comprising an array of pixels and operable to render a pixelated image accordingly; a light field shaping layer (LFSL) defined by an array of LFSL elements and disposed relative to said digital display medium so to dispose each of said LFSL elements over an underlying set of said pixels to shape a light field emanating therefrom and thereby at least partially govern a projection thereof from said display medium toward the viewer; and a hardware processor operable on pixel data for a selected portion of the input image to output adjusted image pixel data to be rendered via said digital display medium and projected through said LFSL so to produce a designated image perception adjustment for said selected portion to at least partially address the viewer's reduced visual acuity when viewing said selected portion.

In one embodiment, the selected portion comprises a text portion.

In one embodiment, the adjusted image pixel data comprises adjusted font pixel data for each text font character in said text portion, to be rendered via said digital display medium and projected through said LFSL so to produce vision corrected font characters that at least partially address the viewer's reduced visual acuity.

In one embodiment, the adjusted font pixel data corresponds to an adjusted font pixel pattern that, when projected through said LFSL, renders a vision corrected text font character.

In one embodiment, the adjusted font pixel pattern is stored and retrieved from a digital adjusted font pattern library as a function of a corrective power defined at least in part by the viewer's reduced visual acuity.

In one embodiment, the pixel data for pixels not associated with said selected portion is adjusted to increase a background contrast with said selected portion.

In one embodiment, the selected portion is automatically selected via said hardware processor.

In one embodiment, the hardware processor is operable to: digitally map said selected portion on an adjusted image plane designated to provide the viewer with the designated image perception adjustment; associate said adjusted image pixel data with at least some of said pixel sets according to said mapping; and render said adjusted image pixel data via said pixel sets thereby rendering a perceptively adjusted version of said selected portion when viewed through said LFSL.

In one embodiment, the adjusted image plane is a virtual image plane virtually positioned relative to said digital display medium at a designated minimum viewing distance designated such that said perceptively adjusted version of said selected portion is adjusted to accommodate the viewer's reduced visual acuity.

In one embodiment, the adjusted image plane is designated as a user retinal plane, wherein said mapping is implemented by scaling said selected portion on said retinal plane as a function of an input user eye focus aberration parameter.

In accordance with another aspect, there is provided a computer-implemented method, automatically implemented by one or more digital processors, to adjust user perception of a selected portion of an input image to be rendered on a digital display via a set of pixels thereof, wherein the digital display has a light field shaping layer (LFSL) disposed thereon comprising an array of LFSL elements, the method comprising: digitally mapping the selected portion of the input image on an adjusted image plane designated to provide the user with a designated image perception adjustment thereof; associating adjusted image pixel data with at least some of said pixel sets according to said mapping to render a perceptively adjusted version of the selected portion; and rendering said adjusted image pixel data via said pixel sets thereby rendering a perceptively adjusted version of the selected portion when viewed through said LFSL.

In one embodiment, the selected portion comprises a text portion, and wherein said digitally mapping comprises mapping said text portion.

In accordance with one aspect, there is provided a digital display device to render an image for viewing by a viewer having reduced visual acuity, the device comprising: a digital display medium for rendering the image based on pixel data related thereto; a complementary light field display portion; and a hardware processor operable on said pixel data for a selected portion of the image to be rendered via said complementary light field display portion so to produce vision-corrected pixel data corresponding thereto to at least partially address the viewer's reduced visual acuity when viewing said selected portion as rendered in accordance with said vision-corrected pixel data by said complementary light field display portion.

In one embodiment, the complementary light field display portion comprises a distinctly operated light field display medium.

In one embodiment, the complementary light field display is mechanically segregated from said digital display medium within a common digital display device housing.

In one embodiment, the distinctly operated light field display medium is detachably coupled to said digital display medium.

In one embodiment, the distinctly operated light field display is pivotably coupled relative to said digital display medium so to selectively form an angle relative thereto.

In one embodiment, the complementary light field display portion comprises a distinctly addressable portion of said digital display medium.

In one embodiment, the device comprises a touch sensitive graphical user interface rendered by said digital display medium, and wherein said selected portion is selected in response to a selective viewer input received via said touch sensitive graphical user interface.

In one embodiment, the device comprises an external user interface external to said digital display medium, and wherein said selected portion is selected in response to a selective viewer input received via said external interface.

In one embodiment, the selective viewer input comprises a scrolling, sliding or panning action resulting in a corresponding scrolling, scanning or panning of said selected portion.

In one embodiment, the digital display device further comprises one or more viewer-facing cameras for tracking an viewer eye or pupil location, wherein said hardware processor is further operable to adjust said vision-corrected portion based on said viewer eye or pupil location.

In one embodiment, the one or more viewer-facing cameras are operatively mounted adjacent said complementary light field display.

In one embodiment, the image comprises text, and wherein said vision-corrected portion comprises vision-corrected text.

In one embodiment, the vision-corrected text is restricted to vision-corrected font portions.

In one embodiment, the hardware processor is operable on pixel data to output corrective font pixel data to be rendered via said complementary light field display, wherein said corrective font pixel data for distinct text characters in the text corresponds to distinct corrective light field font pixel patterns that, when viewed via said light field display, render distinct vision corrected text characters accordingly.

In one embodiment, each of said distinct corrective light field font pixel patterns in the text is stored and retrieved from a digital corrective font pattern library.

In one embodiment, the distinct corrective light field font pixel patterns are stored as a function of a corrective power defined at least in part by the viewer's reduced visual acuity.

In one embodiment, the digital display device comprises one of a mobile phone, a smartphone, a tablet, or an e-reader.

In one embodiment, the selective viewer input is associated with a digital pointer selectively operable by the viewer to select said portion, wherein said portion is defined by an area on said digital display medium corresponding with a digital pointer location on said digital display medium.

In accordance with another aspect, there is provided a visual aid device for cooperative coupling to a digital display to render a selected portion of an image rendered thereon to be viewed by a viewer having reduced visual acuity, the device comprising: a complementary light field display to be operatively coupled to the digital display device and to receive therefrom pixel data associated with the selected portion of the image to be rendered via said complementary light field display; and a hardware processor operable on said pixel data to produce a vision-corrected portion of the image corresponding to the selected portion that at least partially addresses the viewer's reduced visual acuity when viewing said vision-corrected portion as rendered by said complementary light field display.

In one embodiment, the visual aid device further comprises one or more viewer-facing cameras for tracking a viewer eye or pupil location, wherein said hardware processor is further operable to adjust said vision-corrected portion based on said viewer eye or pupil location.

In one embodiment, the hardware processor is further operable to: identify a text area to be correctively rendered; define corrective font pixel data to be rendered via said light field display so to produce vision-corrected text; and render the corrective font pixel data so to produce said vision-corrected text to at least partially address the viewer's reduced visual acuity.

In one embodiment, the defining comprises defining said corrective font pixel data for distinct text characters in the text to correspond to distinct corrective light field font pixel patterns that, when projected through said light field display, render distinct vision corrected text characters accordingly.

In one embodiment, the identifying comprises automatically recognizing said distinct text characters, and wherein said defining comprises retrieving from digital storage said distinct corrective light field font pixel patterns corresponding to said automatically recognized text characters.

In one embodiment, the defining comprises executing a digitally implemented ray-tracing process to: digitally map the text on an adjusted image plane designated to at least partially address the viewer's reduced visual acuity; and associate said corrective font pixel data with corresponding pixels according to said mapping and a physical geometry of the display medium and the viewer.

In one embodiment, the adjusted image plane is a virtual image plane virtually positioned relative to the digital display at a designated distance from the viewer.

In one embodiment, the designated distance comprises a minimum viewing distance designated a function of the viewer's reduced visual acuity.

In one embodiment, the adjusted image plane is designated as a user retinal plane.

In one embodiment, the complementary light field display comprises a pixelated image rendering medium and an array of light field shaping elements disposed relative thereto.

In one embodiment, the light field shaping elements form at least one of a microlens array or a parallax barrier.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 5 is process flow diagram of an illustrative ray-tracing rendering process, in accordance with another embodiment;

Figure 1C:
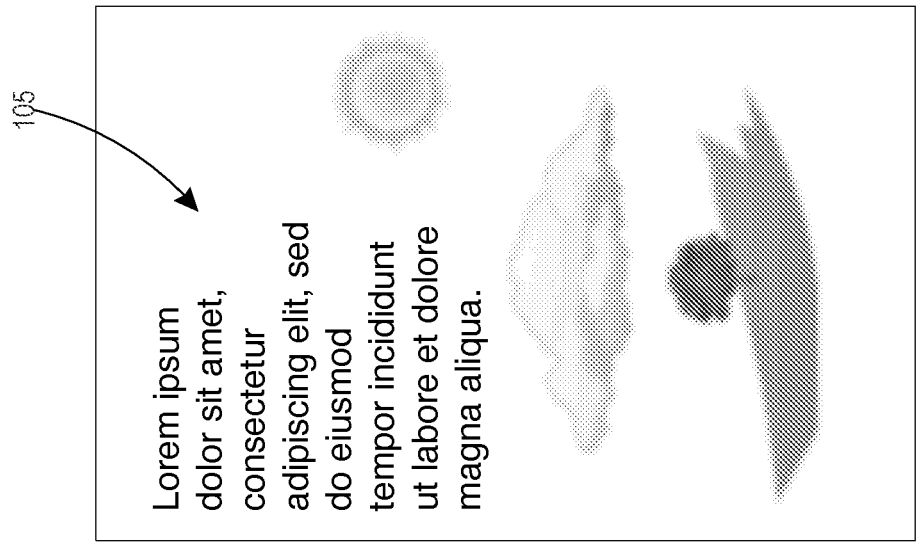
FIGS. 1A to 1C are schematic diagrams illustrating a selective light field rendering process as perceived by a user having reduced visual acuity, in accordance with one embodiment.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

The systems and methods described herein provide, in accordance with different embodiments, different examples of a digital display device comprising a complementary light filed display or display portion, and vision correction system and method using same. For instance, the devices, displays and methods described herein may allow a user's perception of an input image to be displayed, to be adjusted or altered selectively using the complementary light field display or portion. In some examples, users who would otherwise require corrective eyewear such as glasses or contact lenses, or again bifocals, may consume images, or portions thereof, produced by such devices, displays and methods in clear or improved focus without the use of such eyewear. Other light field display applications, such as 3D displays and the like, may also benefit from the solutions described herein, and thus, should be considered to fall within the general scope and nature of the present disclosure.

For example, some of the herein described embodiments provide for digital display devices, or devices encompassing such displays, for use by users having reduced visual acuity, whereby images, or portions thereof ultimately rendered by such devices can be dynamically processed and rendered via a complementary light field display or display portion to accommodate the user's reduced visual acuity so that they may consume such image portions of the input image without the use of corrective eyewear, as would otherwise be required. As noted above, embodiments are not to be limited as such as the notions and solutions described herein may also be applied to other technologies in which a user's perception of selected features and/or image portions of an input image to be displayed can be altered or adjusted via the light field display.

Nonetheless, for the sake of describing illustrative embodiments, greater attention will be drawn to examples in which a selected portion to be rendered by the complementary light field display portion is dedicated to a text portion, or again a selected text portion of a greater full screen text image, for example, as may be commonly rendered on electronic reading devices or the like.

Figure 1B:
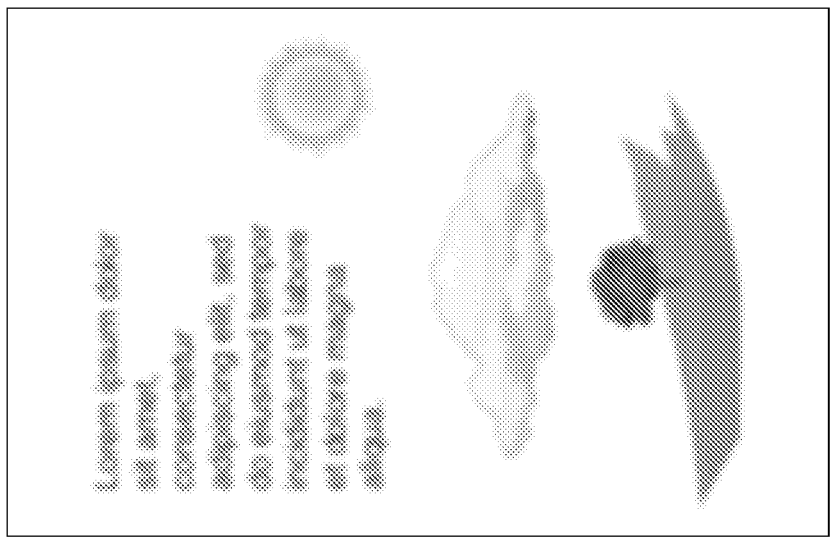
Figure 1A:
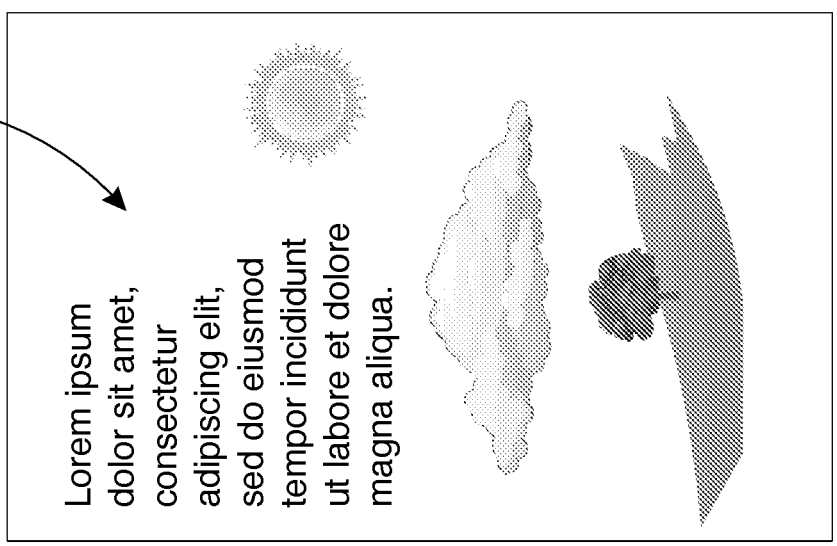

With reference to FIGS. 1A to 1C, and in accordance with one embodiment, an example of a light field display, such as those exemplarily described herein, is operated to selectively accommodate a user's reduced visual acuity by adjusting via light field only selected features and/or image portions of an input digital image. For example, FIG. 1A shows an exemplary input digital image comprising a multiplicity of features, including an image portion 105 comprising text. When viewed by a user having reduced visual faculties, the image is perceived as blurry as shown in FIG. 1B. While the entire input digital image may be rendered via a light field to accommodate the user's reduced visual faculty, as detailed for example in Applicant's co-pending U.S. application Ser. No. 16/259,845, filed Jan. 28, 2019, the entire contents of which are hereby incorporated herein by reference, in some cases, it may be preferable to provide an enhancement only to selected features and/or image portions. For example, and as illustrated in FIG. 1C, the device can be operated to only provide an accurate vision correction augmentation for the selected image portion (e.g. herein text-rich region 105), while only providing a partial or no vision correction for the rest of the image (as will be explained below). Indeed, image correction may be limited to the text-rich portion of the input image, or again, limited in fact only to the pixels involved in rendering vision corrected fonts, which, in some embodiments, may be designated to render vision corrected font patterns that, when projected through the LFSL, result in vision corrected text. As detailed below, these vision corrected font patterns may be defined in real-time as a result of an onboard ray tracing engine that accounts for various operational parameters such as for example, but not limited to, LFSL characteristic(s), a tracked viewer pupil location, vision correction parameter(s), etc., and/or again, at least partially defined and retrieved from persistently or temporarily stored corrective font pattern libraries or similar data storage structures.

Using this approach, and increasingly so in the latter scenario of image corrected fonts, only a relatively small subset of image pixels need be addressed by the image correction application, whereas surrounding pixels (typically invoking limited if any image detail beyond a background colour), can be rendered unaltered, thus significantly reducing a processing load that would otherwise be associated therewith.

In one embodiment, the image correction application may be executed within the context of an electronic device predominantly used to display text or text-rich images, such as for example, an electronic reader, or again a mobile phone, smartphone or other like smart devices used predominantly for consuming text messages, emails, social media posts and/or browsing text-rich online content, for example. For such implementations, a user may indeed wish to invoke corrective text or font features of the device to improve their ability to consume text, without necessarily requiring vision correction applications to other screen image components. For example, a user wishing to consume multimedia content on their device (e.g. images or video content on a smartphone, tablet or laptop computer) may prefer to wear corrective lenses, whereas this user may wish to invoke the ability to quickly consume vision corrected text-rich content on-the-fly without reaching for their corrective lenses. Other user scenarios may readily apply, as will be readily appreciated by the skilled artisan, without departing from the general scope and nature of the present disclosure.

In the end, methods such as those considered herein may provide viewers the ability to correctly perceive the most important part of the input images being rendered on their devices (e.g. the selected portion or text), without necessarily requiring full corrective image processing otherwise required for full digital image correction.

For example, in some embodiments as further described below, a dynamic ray tracing process may be invoked to dynamically compute corrective pixel values required to render a corrective image portion that can accommodate a viewer's reduced visual acuity. Accordingly, by limiting the selected portion of interest, a reduced computation load may be applied to the device.

Indeed, in some embodiments, significant computational load reductions may be applied where the device can predictively output designated text-based corrections given an average relative text and/or viewer pupil location, invoking ray tracing in some instances only where significant positional/orientation changes are detected, if at all required in some embodiments and/or implementations.

In yet other embodiments invoking corrective text or corrective font functions, a set of designated pixelated corrective font patterns may be preset and stored on the device such that, when the device is called upon to render a particular character, the designated pixelated corrective font pattern for this character may be retrieved (e.g. from a stored corrective font pattern library) and rendered automatically without, or with minimal ray tracing requirements. For instance, depending on the nature of the application at hand, typical usage configurations (e.g. distance, orientation, motion in use, etc.), the corrective power required (e.g. significant or light visual acuity correction), or the like, different corrective font libraries or sets may be stored accordingly to directly accommodate corrective text rendering while invoking reduced if not entirely bypassing ray tracing requirements.

Figure 11:
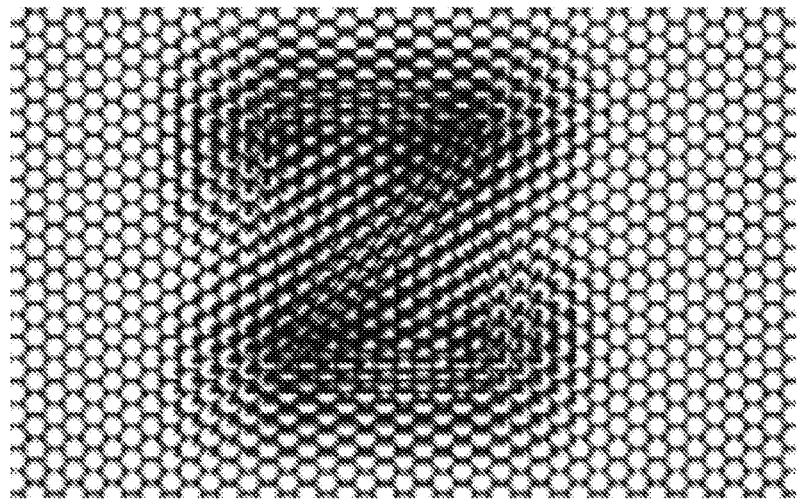
FIG. 11 is an exemplary diagram of a vision corrected light field pattern that, when properly projected by a light field display, produces a vision corrected rendering of the letter "Z" exhibiting reduced blurring for a viewer having reduced visual acuity, in accordance with one embodiment.
Figure 12A:
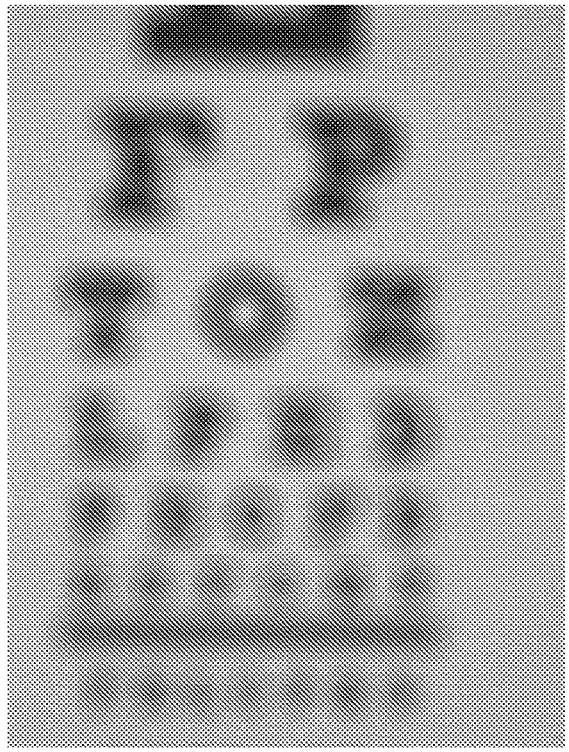
FIGS. 12A and 12B are photographs of a Snellen chart, as illustratively viewed by a viewer with reduced acuity without image correction (blurry image in FIG. 12A) and with image correction via a light field display (corrected image in FIG. 12B), in accordance with one embodiment.
Figure 12B:
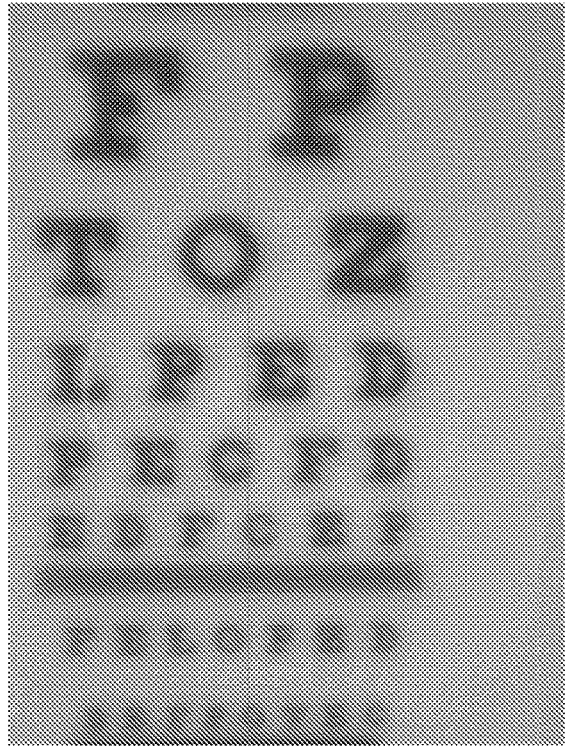

For example, upon predictably aligning a particular light field shaping layer (LFSL), such as a microlens array, with a pixel array, a designated "circle" of pixels will correspond with each microlens and be responsible for delivering light to the pupil through that lens. In one such example, a light field display assembly comprises a microlens array that sits above an LCD display on a cellphone or portable display device to have pixels emit light through the microlens array. A ray-tracing algorithm can thus be used to produce a pattern to be displayed on the pixel array below the microlens in order to create the desired virtual image that will effectively correct for the viewer's reduced visual acuity. FIG. 11 provides an example of such a pattern for the letter "Z", which, when viewed through a correspondingly aligned microlens array, will produce a perceptively sharp image of this letter to a viewer having a correspondingly reduced visual acuity. Accordingly, by storing such patterns, or reconstructive information related thereto, in a corrective font pattern library or like data repository, for all characters that may be required to display corrective text, these patterns can be selectively aligned to reconstruct an input text in outputting a vision-corrective text output that can be effectively viewed by a viewer having reduced visual acuity without the need for corrective eyewear. Leveraging a corrective font "pattern" library as noted above may thus, in some embodiments, allow for a reduction in ray tracing and/or pupil tracking capabilities, albeit possibly in exchange for some loss in corrective output quality, accuracy and/or accommodation efficiency.

In yet other embodiments, for example where pupil position and/or distance tracking is not readily available, dynamic corrective font set selection may be adjustably provided to the viewer so that they may dynamically test various particular corrective font sets until a best set is identified (i.e. the corrective font set that best addresses their reduced visual acuity, average reading distance, etc.). Naturally, without dynamic pupil tracking, a viewer may be more likely to accommodate a particular corrective font selection by substantially maintaining a particular viewing distance, position and/or configuration. These and other such considerations are deemed to fall within the general nature and context of the present disclosure.

In some embodiments, the information describing which elements to designate as selected features and/or image portions may be encoded directly into the input image. In the case of text, for example, a software font engine in the form of a proprietary and/or shared library, or similar (e.g. similar to a font rasterizing library) may be used to help render vision corrected fonts. Such a shared corrective font library may be built into the operating system or the desktop environment of the electronic device, may be added later, or again accessed on-the-fly through an available network interface. This font engine may be operable to accept/intercept font rendering (rasterization) commands and for example send directly to the light field rendering engine to be rendered preferentially via light field optimization.

Generally speaking, the skilled technician will understand that selected features and/or image portions other than text or text-rich portions may be chosen. As discussed below, the information describing these features and/or image portions may be encoded directly in the input digital image and/or may be determined using a detection engine, as described below. For example, the selected features may comprise complex symbols and/or pictograms, for example in the context of displaying information in a vehicular setting or similar. In yet other examples, selected features may comprise edges and/or dark lines when viewing images, such as 2D line drawings and/or sketches.

In some embodiments, a light field rendering detection engine may be used for detecting one or more image portions within an input digital image to be preferentially rendered via a light field by the light field display. In one example, the system may receive the digital image data to be displayed and may use the detection engine to analyze the features inside the digital image data and identify therein the image portions to be rendered preferentially by the light field. In some embodiments, an image portion may comprise pictures, illustrations, text, individual letters/symbols or the like. In some embodiments, the detection engine may use any pattern recognition algorithm known in the art. These may include, without limitation, any supervised or unsupervised machine learning methods known in the art.

In some embodiments, the detection engine may operate in real-time while in some embodiments, the input image may be pre-processed by the detection engine separately to generate a new digital image data file further comprising/encoding any information about the selected features/image portions. This new file may be then stored to be used by the light field display at a later time.

For example, in a corrective text or font embodiment, a new image data file may resemble, comprise or be derived from a reader mode or reader view file in which text-based content is isolated and/or manipulated whereas other content (buttons, ads, multimedia content, background images, etc.) is dismissed or redacted. In doing so, inbound image data can be effectively parsed to isolate text-based content of interest, which can (concurrently or sequentially) itself be processed for corrective purposes, whereby display portions not involved in the display of corrective text can be advantageously dismissed for further processing (e.g. by rendering a basic background colour).

In some of the herein-described embodiments, a selected image portion may be correctively rendered via a complementary light field display in that, rather than to produce corrective image pixel data to be rendered via a full scale light field display, a selected portion of the image to be rendered via a standard digital display device can be relayed to a complementary light field display for corrective rendering, or again, rendered via a distinctly addressable light field display portion of the digital display device. In such embodiments, display and image rendering requirements can be reduced as only a subset of the rendered image pixel data may be processed for light field rendering, and that, via a smaller, high pixel density, light field display or light field display portion. As illustrated in the illustrative embodiments described below, a complementary light field display may be physically integrated with a main digital display medium within a same digital display device, and that, in a fixed or retractable configuration, or again provided as a separate but cooperatively operable light field display, in each case operable to render a vision or otherwise light field corrected image portion to the viewer, such portions including, but not limited to, a selected text or reading portion, or the like. Similarly, a dedicated portion of the digital display device's display medium may be distinctly addressable to produce a light field display portion thereof, for example, via a dedicated array of light field shaping elements disposed in relation to this portion, or again, by distinctly addressing a selected or dedicated portion of a full light field display. Examples are provided below as to different complementary light field display configurations in which the complementary light field display portion is distinctly provided and operated in cooperation with a main digital display medium.

It will nonetheless be appreciated that similar embodiments may encompass distinctly addressable light field display portions of a larger display medium to provide similar effects and benefits, as noted above, without departing from the general scope and nature of the present disclosure.

Figure 13A:
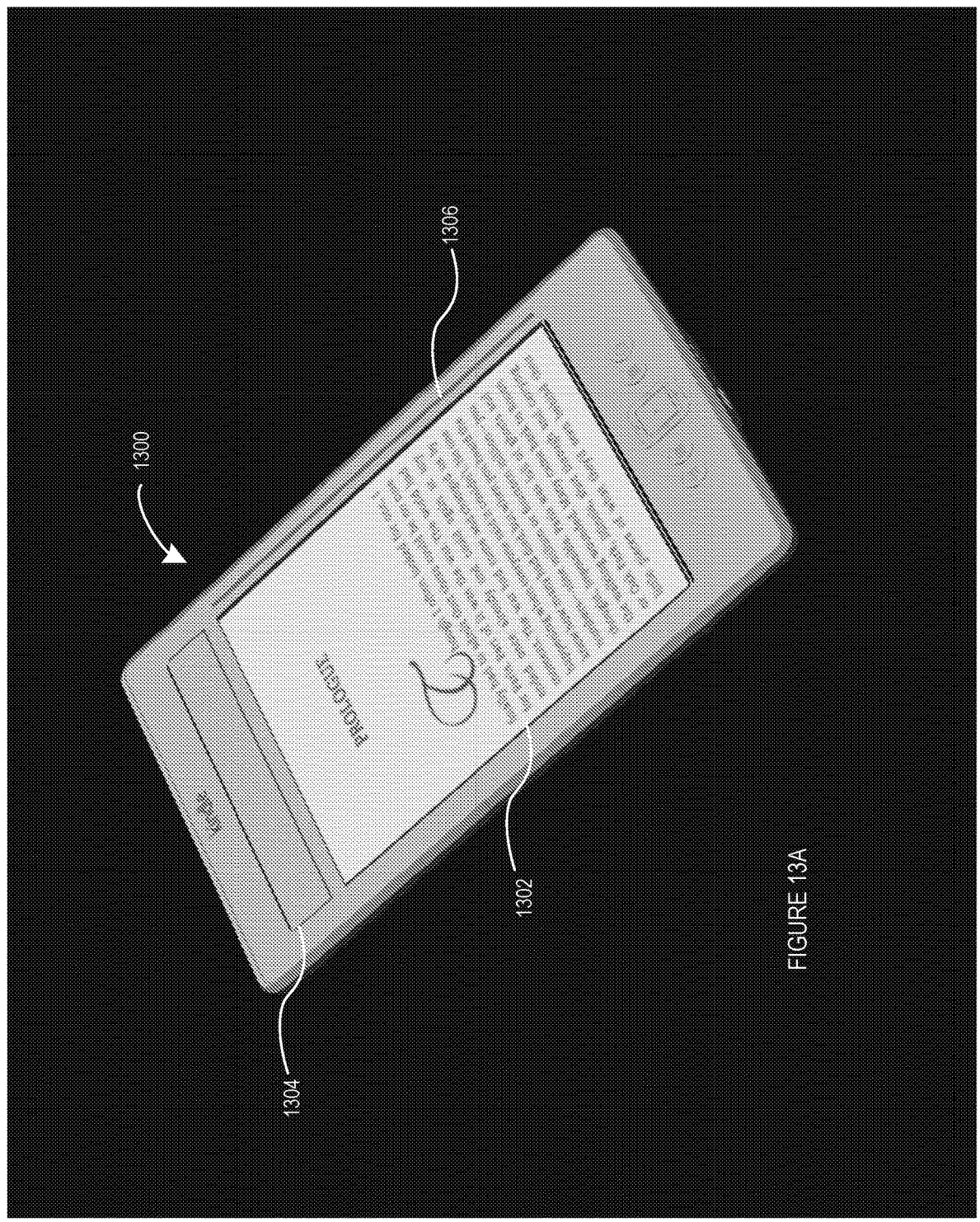
FIGS. 13A and 13B are diagrams of a digital display device having a complementary light field display in each of a retracted and active configuration, respectively, and an integrated touch-sensitive user interface, in accordance with one embodiment.
Figure 13B:
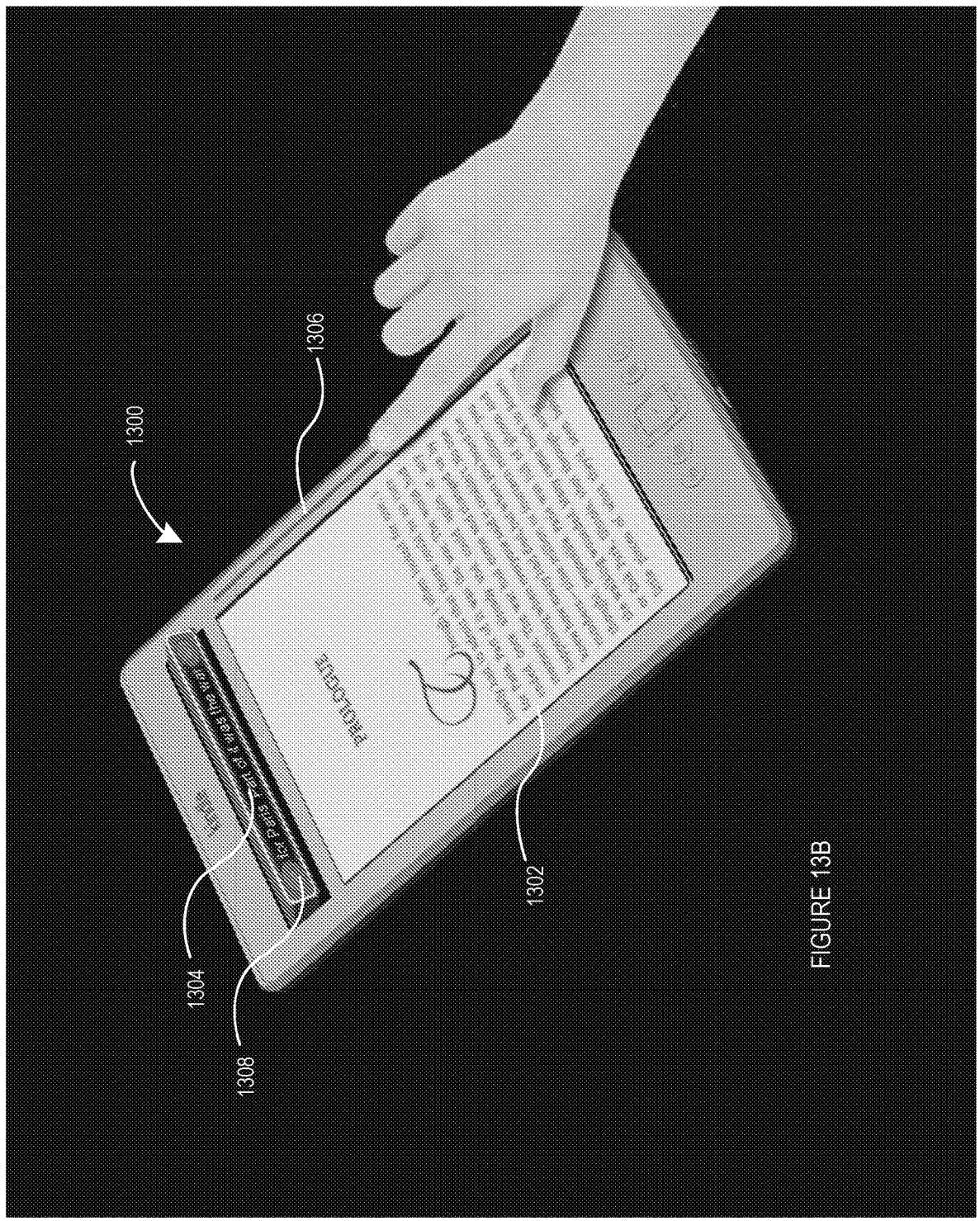

With reference to FIGS. 13A and 13B, and in accordance with one embodiment, a digital e-reader 1300 generally comprises a main digital image display 1302 on which to display a rendered text. The e-reader also comprises a retractable complementary light field display 1304 shown in retracted and active configurations in FIGS. 13A and 13B, respectively. Namely, the illustrated light field display 1304 can be retracted and operated at a 45 degree angle relative to the main display 1302 so to render vision corrected text corresponding to a portion of the full text rendered on the main display. For example, in this embodiment, the e-reader comprises a touch-activated sensor 1306, or like user interface, that can be operated to receive as input a user selection of a text portion of interest, such as one or more text lines corresponding to a location of the user touch selection, which text lines can then be relayed to the light field display for corrective rendering. As further detailed herein, the selected text portion may be relayed in its native form and processed by a distinct vision correction processor or engine that can operate on pixel data related to the text portion to produce vision corrected text, such as via an implemented pixel or subpixel-based ray tracing algorithm, corrective font pattern rendering process, or the like. The corrective light field pixel data can otherwise be processed by the native or core processor of the device and operatively related to the light field display for corrective rendering.

In the illustrated embodiment, the extractable light field display is also paired with a pair of viewer-facing cameras 1308 that can be operated to track a viewer eye or pupil location and adjust a corrective rendering on the light field display accordingly. For example, a tracked eye or pupil location can be used as input in a ray tracing algorithm to compute corrective pixel data to be rendered via the light field display. In other embodiments, active eye or pupil tracking may be omitted and rather rely on predictive or typical viewer eye or pupil locations/distances. For example, in some embodiments, a user may actively or dynamically adjust the corrective display based on a general view distance, with the expectation that the viewer will typically view the device at roughly normal incidence.

Figure 14:
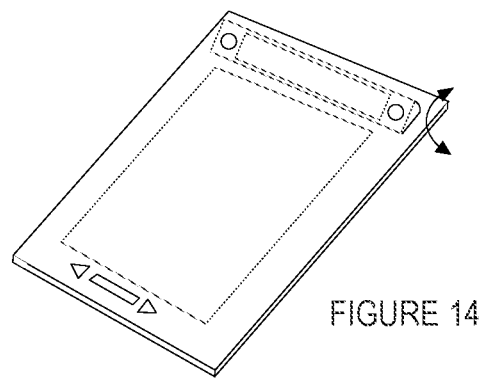
FIG. 14 is a diagram of a digital display device having a retractable complementary light field display and integrated eye or pupil tracking optics, in accordance with another embodiment.

With reference to FIG. 14, another example of an assistive e-reader is illustrated in which a complementary light field display is shown to pivot between a retracted and active configuration. In this embodiment, unlike the embodiment of FIGS. 13A and B, an external user interface is not provided for text selection. Instead, a user selection can be identified via the touch screen interface of the e-reader, directly. In some implementations, the portion selection may be directly or indirectly linked to other device functions or interfaces, for example, whereby a selection is automatically executed and changed as the rendered text migrates or moves across the screen. For example, in a scrolling mode, the selected text portion may be selected as the top one or more lines rendered on the screen, or again, the last one or more lines to scroll off the screen, i.e. continuously scrolling into the light field display. These and other dynamic image/text portion selection mechanism may be considered herein without departing from the general scope and nature of the present disclosure.

In other embodiments, an image or text portion selection may be automatically implemented for certain features or functions of the digital display device. For example, in some embodiments, certain notifications (e.g. alerts, inbound texts, email captions, etc.) may be automatically routed to the vision correcting light field display. In such operational modes, a viewer who is otherwise not actively using or reading their device output may nonetheless receive the pushed notification and view them without reaching for the correctively eyewear, for example. This may be particular useful in a smartphone implementation, where a user may wish to reach for their device to consume a recent notification without necessarily reaching for their glasses as they would otherwise to consult the full device display for a prolonged period.

Figure 15:
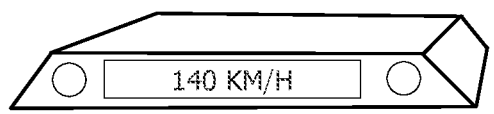
FIG. 15 is a diagram of an externally mounted complementary light field display operatively coupled to a vehicular dashboard or operator display, in accordance with one embodiment.
Figure 16A:
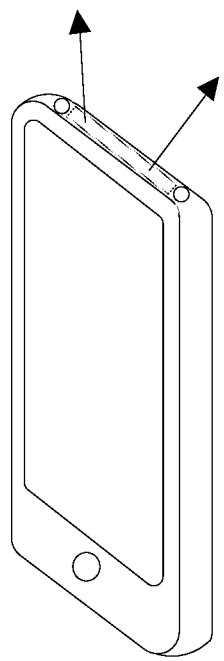
FIGS. 16A and 16B are diagrams of a smartphone device and longitudinally extractable complementary light field display, respectively, in accordance with one embodiment.
Figure 16B:
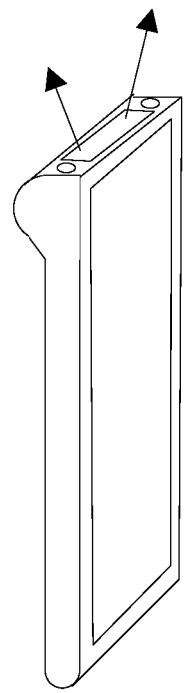

With reference to FIGS. 15A and 15B, a smartphone embodiment is illustrated in which a main smartphone device as shown in FIG. 15A comprises an inset longitudinally extractable light field display that is operable as described above with respect to the noted e-reader embodiments. Similarly, with reference to FIGS. 16A and 16B, another smartphone embodiment is illustrated in which a main smartphone device as shown in FIG. 16A comprises an inset laterally extractable light field display that is operable as described above with respect to the noted e-reader embodiments. In these embodiments, an image or text portion selection may be executed via the devices main touch screen interface, or again via a related external interface. For instance, one or more lines of text may be dynamically selected around a touchscreen location selected by the user, or again, may take the form of a zoomed-in or adapted vision correction bubble or the like that allows the user to consult various selective portions of the uncorrected image. In these or other embodiments, the extractable light field display screen may be configured to project corrective text, images, icons or indicia related to a latest one or more notifications, text messages and/or emails, as the case may be.

As in the above noted examples, the light field display, or device itself, may include associated therewith one or more viewer-facing cameras or like optical devices to track the viewer's eye or pupil location to optimize the correctively light field output.

In some embodiments, the user may have access to certain user customization features or functions so to select which information is automatically relayed to the vision corrected display, and/or in which circumstances. For example, much as a viewer can customize their notification center on certain mobile/smartphone devices, so could a viewer selectively define which information to automatically push or display on the vision corrected screen. As such, a user that would otherwise typically require reading glasses to consume digital data on their device, could automatically activate their vision corrected notification center on the extractable screen to consume selected notifications without the use of corrective eyewear, such as recent texts, messages, time, date, weather, and other application-specific notifications. These or other such options are intended to fall with the general scope and nature of the present disclosure.

Figure 17A:
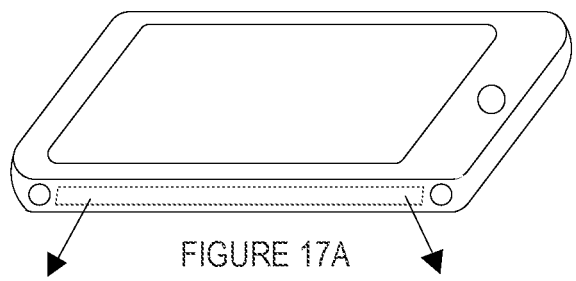
FIGS. 17A and 17B are diagrams of a smartphone device and laterally extractable light field display, respectively, in accordance with another embodiment.
Figure 17B:
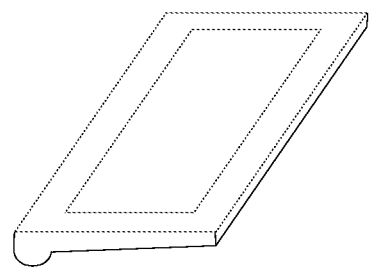

With reference to FIG. 17, an external complementary light field display is illustrated for operation, for example, within the context of an automotive display, in which a selected or dedicated portion of an automotive display or dashboard is selectively rendered in vision corrected form. For example, an integrated or detachably coupled light field device may be mounted or manufactured in the driver's field of view and operated to render a vision corrected portion of the vehicles display(s), such as dashboard controls, status and operational information, multimedia controls, or the like. As in the above noted examples, the light field display may include associated therewith one or more viewer-facing cameras or like optical devices to track the viewer's eye or pupil location to optimize the corrective light field output.

In some embodiments, light field rendering and/or eye/pupil tracking data can be centrally computed by a central processing unit of the digital display device (e.g. e-reader, tablet or smartphone processing unit), whereas in other embodiments, light field and/or eye/pupil tracking processing can be executed by a distinct vision correction processor and/or engine. In such latter embodiments, native image content or pixel data can be relayed to the light field rendering processor and display for processing. In one such latter embodiment, the vision correction hardware is detachably coupled to the native digital display device in that an extractable or otherwise complementary light field display is mechanically and/or electronically coupled to the device to cooperate therewith. In such embodiments, distinct processing resources may access data related to the selected portion via a communication interface with the native digital display device, as can various cooperative user interfaces be defined to identify and select a display portion of interest. Interfacing software or like application protocol interfaces (APIs) may be leveraged to gain access to display content (portions), notifications, etc. that are to be vision corrected. Such communicative interfaces may be hardwired through one or more digital display device ports, and/or via one or more wireless interface such as near field communication (NFC), Bluetooth™, Wi-Fi, etc.

Generally, digital light field displays as considered herein will comprise a set of image rendering pixels and a light field shaping layer disposed or integrated at a preset distance therefrom so to controllably shape or influence a light field emanating therefrom. For instance, each light field shaping layer will be defined by an array of optical elements centered over a corresponding subset of the display's pixel array to optically influence a light field emanating therefrom and thereby govern a projection thereof from the display medium toward the user, for instance, providing some control over how each pixel or pixel group will be viewed by the viewer's eye(s). As will be further detailed below, arrayed optical elements may include, but are not limited to, lenslets, microlenses or other such diffractive optical elements that together form, for example, a lenslet array; pinholes or like apertures or windows that together form, for example, a parallax or like barrier; concentrically patterned barriers, e.g. cut outs and/or windows, such as a to define a Fresnel zone plate or optical sieve, for example, and that together form a diffractive optical barrier (as described, for example, in Applicant's co-pending U.S. application Ser. No. 15/910,908, the entire contents of which are hereby incorporated herein by reference); and/or a combination thereof, such as for example, a lenslet array whose respective lenses or lenslets are partially shadowed or barriered around a periphery thereof so to combine the refractive properties of the lenslet with some of the advantages provided by a pinhole barrier.

In operation, the display device will also generally invoke a hardware processor operable on image pixel (or subpixel) data for an image to be displayed to output corrected or adjusted image pixel data to be rendered as a function of a stored characteristic of the light field shaping layer (e.g. layer distance from display screen, distance between optical elements (pitch), absolute relative location of each pixel or subpixel to a corresponding optical element, properties of the optical elements (size, diffractive and/or refractive properties, etc.), or other such properties, and a selected vision correction or adjustment parameter related to the user's reduced visual acuity or intended viewing experience. While light field display characteristics will generally remain static for a given implementation (i.e. a given shaping layer will be used and set for each device irrespective of the user), image processing can, in some embodiments, be dynamically adjusted as a function of the user's visual acuity or intended application so to actively adjust a distance of a virtual image plane, or perceived image on the user's retinal plane given a quantified user eye focus or like optical aberration(s), induced upon rendering the corrected/adjusted image pixel data via the static optical layer, for example, or otherwise actively adjust image processing parameters as may be considered, for example, when implementing a viewer-adaptive pre-filtering algorithm or like approach (e.g. compressive light field optimization), so to at least in part govern an image perceived by the user's eye(s) given pixel or subpixel-specific light visible thereby through the layer.

Accordingly, a given device may be adapted to compensate for different visual acuity levels and thus accommodate different users and/or uses. For instance, a particular device may be configured to implement and/or render an interactive graphical user interface (GUI) that incorporates a dynamic vision correction scaling function that dynamically adjusts one or more designated vision correction parameter(s) in real-time in response to a designated user interaction therewith via the GUI. For example, a dynamic vision correction scaling function may comprise a graphically rendered scaling function controlled by a (continuous or discrete) user slide motion or like operation, whereby the GUI can be configured to capture and translate a user's given slide motion operation to a corresponding adjustment to the designated vision correction parameter(s) scalable with a degree of the user's given slide motion operation. These and other examples are described in Applicant's co-pending U.S. patent application Ser. No. 15/246,255, the entire contents of which are hereby incorporated herein by reference.

In general, a digital display device as considered herein may include, but is not limited to, smartphones, tablets, e-readers, watches, televisions, GPS devices, laptops, desktop computer monitors, televisions, smart televisions, handheld video game consoles and controllers, vehicular dashboard and/or entertainment displays, ticketing or shopping kiosks, point-of-sale (POS) systems, workstations, or the like.

Generally, the device will comprise a processing unit, a digital display, and internal memory. The display can be an LCD screen, a monitor, a plasma display panel, an LED or OLED screen, or any other type of digital display defined by a set of pixels for rendering a pixelated image or other like media or information. Internal memory can be any form of electronic storage, including a disk drive, optical drive, read-only memory, random-access memory, or flash memory, to name a few examples. For illustrative purposes, memory has stored in it a vision correction or image adjustment application and/or a predictive pupil tracking engine, though various methods and techniques may be implemented to provide computer-readable code and instructions for execution by the processing unit in order to process pixel data for an image to be rendered in producing corrected pixel data amenable to producing a corrected image accommodating the user's reduced visual acuity (e.g. stored and executable image correction application, tool, utility or engine, etc.). Other components of the electronic device may optionally include, but are not limited to, one or more rear and/or front-facing camera(s) (e.g. for onboard pupil tracking capabilities), pupil tracking light source, an accelerometer and/or other device positioning/orientation devices capable of determining the tilt and/or orientation of electronic device, or the like.

For example, the electronic device, or related environment (e.g. within the context of a desktop workstation, vehicular console/dashboard, gaming or e-learning station, multimedia display room, etc.) may include further hardware, firmware and/or software components and/or modules to deliver complementary and/or cooperative features, functions and/or services. For example, as previously noted, a pupil/eye tracking system may be integrally or cooperatively implemented to improve or enhance corrective image rendering by tracking a location of the user's eye(s)/pupil(s) (e.g. both or one, e.g. dominant, eye(s)) and adjusting light field corrections accordingly. For instance, the device may include, integrated therein or interfacing therewith, one or more eye/pupil tracking light sources, such as one or more infrared (IR) or near-IR (NIR) light source(s) to accommodate operation in limited ambient light conditions, leverage retinal retro-reflections, invoke corneal reflection, and/or other such considerations. For instance, different IR/NIR pupil tracking techniques may employ one or more (e.g. arrayed) directed or broad illumination light sources to stimulate retinal retro-reflection and/or corneal reflection in identifying and tracking a pupil location. Other techniques may employ ambient or IR/NIR light-based machine vision and facial recognition techniques to otherwise locate and track the user's eye(s)/pupil(s). To do so, one or more corresponding (e.g. visible, IR/NIR) cameras may be deployed to capture eye/pupil tracking signals that can be processed, using various image/sensor data processing techniques, to map a 3D location of the user's eye(s)/pupil(s). In the context of a mobile device, such as a mobile phone, such eye/pupil tracking hardware/software may be integral to the device, for instance, operating in concert with integrated components such as one or more front facing camera(s), onboard IR/NIR light source(s) and the like. In other user environments, such as in a vehicular environment, eye/pupil tracking hardware may be further distributed within the environment, such as dash, console, ceiling, windshield, mirror or similarly-mounted camera(s), light sources, etc.

Furthermore, the electronic device in this example will comprise a light field shaping layer (LFSL) overlaid or integrated atop a display medium thereof and spaced therefrom (e.g. via an integrated or distinct spacer) or other such means as may be readily apparent to the skilled artisan. For the sake of illustration, the following examples will be described within the context of a light field shaping layer defined, at least in part, by a lenslet array comprising an array of microlenses (also interchangeably referred to herein as lenslets) that are each disposed at a distance from a corresponding subset of image rendering pixels in an underlying digital display. It will be appreciated that while a light field shaping layer may be manufactured and disposed as a digital screen overlay, other integrated concepts may also be considered, for example, where light field shaping elements are integrally formed or manufactured within a digital screen's integral components such as a textured or masked glass plate, beam-shaping light sources or like component. Accordingly, each lenslet will predictively shape light emanating from these pixel subsets to at least partially govern light rays being projected toward the user by the display device. As noted above, other light field shaping layers may also be considered herein without departing from the general scope and nature of the present disclosure, whereby light field shaping will be understood by the person of ordinary skill in the art to reference measures by which light, that would otherwise emanate indiscriminately (i.e. isotropically) from each pixel group, is deliberately controlled to define predictable light rays that can be traced between the user and the device's pixels through the shaping layer.

For greater clarity, a light field is generally defined as a vector function that describes the amount of light flowing in every direction through every point in space. In other words, anything that produces or reflects light has an associated light field. The embodiments described herein produce light fields from an object that are not "natural" vector functions one would expect to observe from that object. This gives it the ability to emulate the "natural" light fields of objects that do not physically exist, such as a virtual display located far behind the light field display, which will be referred to now as the 'virtual image'. As noted in the examples below, in some embodiments, lightfield rendering may be adjusted to effectively generate a virtual image on a virtual image plane that is set at a designated distance from an input user pupil location, for example, so to effective push back, or move forward, a perceived image relative to the display device in accommodating a user's reduced visual acuity (e.g. minimum or maximum viewing distance). In yet other embodiments, lightfield rendering may rather or alternatively seek to map the input image on a retinal plane of the user, taking into account visual aberrations, so to adaptively adjust rendering of the input image on the display device to produce the mapped effect. Namely, where the unadjusted input image would otherwise typically come into focus in front of or behind the retinal plane (and/or be subject to other optical aberrations), this approach allows to map the intended image on the retinal plane and work therefrom to address designated optical aberrations accordingly. Using this approach, the device may further computationally interpret and compute virtual image distances tending toward infinity, for example, for extreme cases of presbyopia. This approach may also more readily allow, as will be appreciated by the below description, for adaptability to other visual aberrations that may not be as readily modeled using a virtual image and image plane implementation. In both of these examples, and like embodiments, the input image is digitally mapped to an adjusted image plane (e.g. virtual image plane or retinal plane) designated to provide the user with a designated image perception adjustment that at least partially addresses designated visual aberrations. Naturally, while visual aberrations may be addressed using these approaches, other visual effects may also be implemented using similar techniques.

Figure 2:
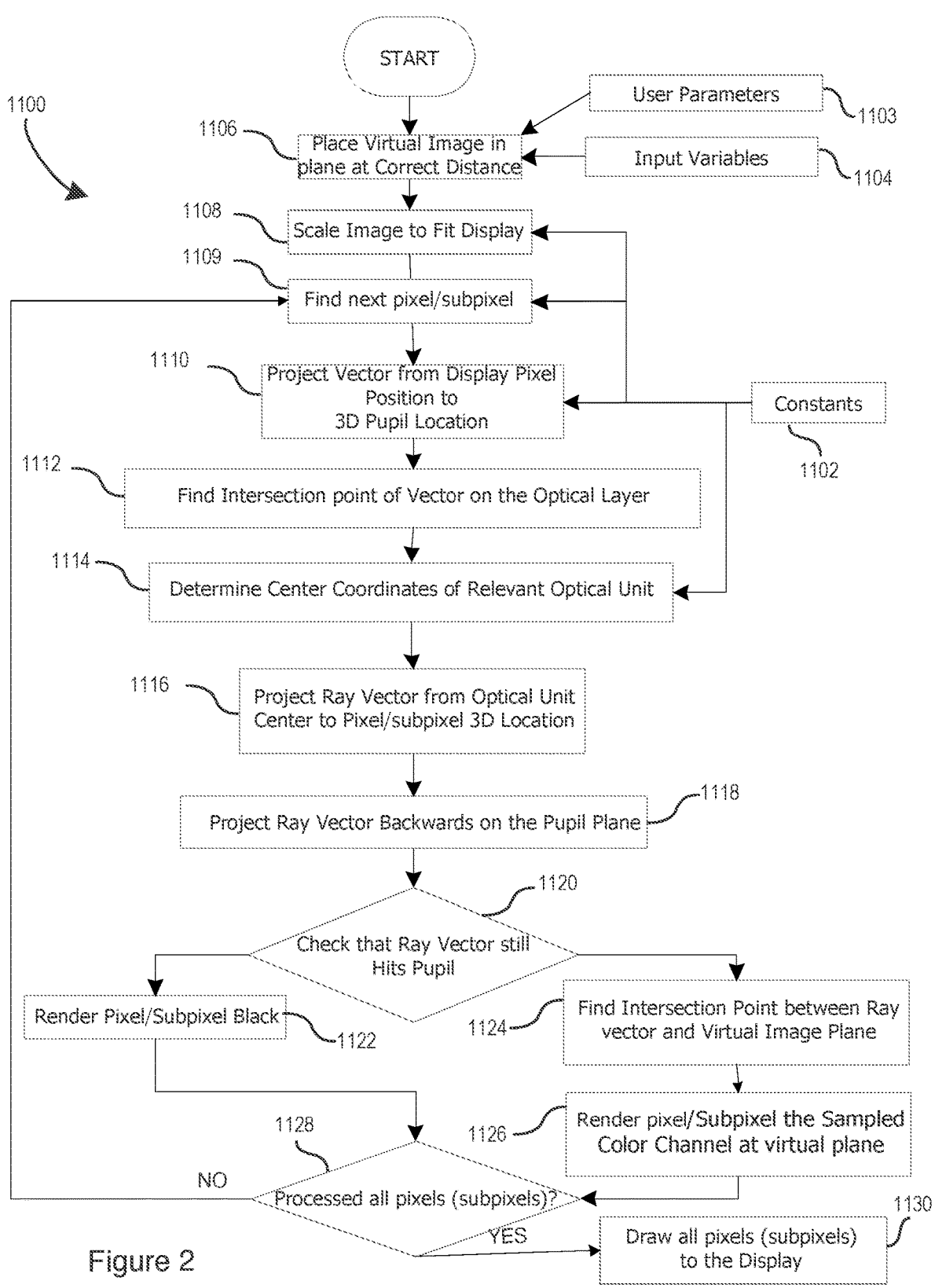
FIG. 2 is a process flow diagram of an illustrative ray-tracing rendering process, in accordance with one embodiment.
Figure 3:
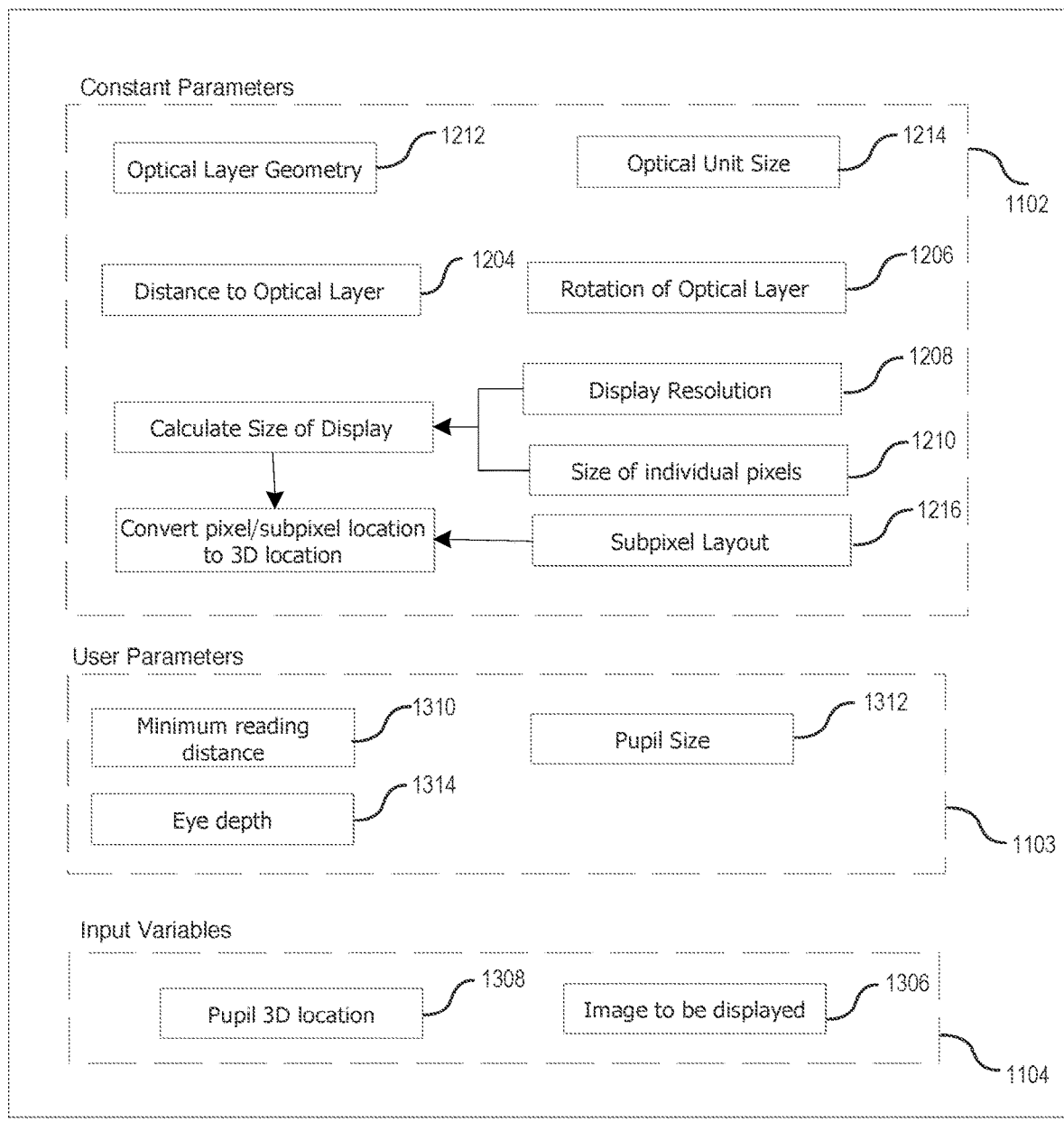
FIG. 3 is a process flow diagram of exemplary input constant parameters, user parameters and variables, respectively, for the ray-tracing rendering process of FIG. 2, in accordance with one embodiment.

With reference to FIGS. 2 and 3, and in accordance with one embodiment, an exemplary, computationally implemented, ray-tracing method for rendering an adjusted image perception via a light field shaping layer (LFSL), for example a computationally corrected image that accommodates for the user's reduced visual acuity, will now be described. In this exemplary embodiment, a set of constant parameters 1102 and user parameters 1103 may be pre-determined. The constant parameters 1102 may include, for example, any data which are generally based on the physical and functional characteristics of the display (e.g. specifications, etc.) for which the method is to be implemented, as will be explained below. The user parameters 1103 may include any data that are generally linked to the user's physiology and which may change between two viewing sessions, either because different users may use the device or because some physiological characteristics have changed themselves over time. Similarly, every iteration of the rendering algorithm may use a set of input variables 1104 which are expected to change at each rendering iteration.

As illustrated in FIG. 3, the list of constant parameters 1102 may include, without limitations, the distance 1204 between the display and the LFSL, the in-plane rotation angle 1206 between the display and LFSL frames of reference, the display resolution 1208, the size of each individual pixel 1210, the optical LFSL geometry 1212, the size of each optical element 1214 within the LFSL and optionally the subpixel layout 1216 of the display. Moreover, both the display resolution 1208 and the size of each individual pixel 1210 may be used to pre-determine both the absolute size of the display in real units (i.e. in mm) and the three-dimensional position of each pixel within the display. In some embodiments where the subpixel layout 1216 is available, the position within the display of each subpixel may also be pre-determined. These three-dimensional location/positions are usually calculated using a given frame of reference located somewhere within the plane of the display, for example a corner or the middle of the display, although other reference points may be chosen. Concerning the optical layer geometry 1212, different geometries may be considered, for example a hexagonal geometry such as the one shown in FIG. 8. Finally, by combining the distance 1204, the rotation angle 1206, and the geometry 1212 with the optical element size 1214, it is possible to similarly pre-determine the three-dimensional location/position of each optical element center with respect to the display's same frame of reference.

In FIG. 3, we also find an exemplary set of user parameters 1103 for method 110, which includes any data that may change between sessions or even during a session but is not expected to change in-between each iteration of the rendering algorithm. These generally comprise any data representative of the user's reduced visual acuity or condition, for example, without limitation, the minimum reading distance 1310, the eye depth 1314 and an optional pupil size 1312. In the illustrated embodiment, the minimum reading distance 1310 is defined as the minimal focus distance for reading that the user's eye(s) may be able to accommodate (i.e. able to view without discomfort). In some embodiments, different values of the minimum reading distance 1310 associated with different users may be entered, for example, as can other vision correction parameters be considered depending on the application at hand and vision correction being addressed. In some embodiments, the minimum reading distance 1310 may also change as a function of the time of day (e.g. morning vs. evening).

FIG. 3 further illustratively lists an exemplary set of input variables 1104 for method 1100, which may include any input data fed into method 1100 that is expected to change rapidly in-between different rendering iterations, and may thus include without limitation: the image(s) to be displayed 1306 (e.g. pixel data such as on/off, colour, brightness, etc.) and the three-dimensional pupil location 1308.

The image data 1306, for example, may be representative of one or more digital images to be displayed with the digital pixel display. This image may generally be encoded in any data format used to store digital images known in the art. In some embodiments, images 1306 to be displayed may change at a given framerate.

Following from the above-described embodiments, as mentioned above, a further input variable includes the three-dimensional pupil location 1308. As detailed above, the input pupil location in this sequence may include a current pupil location as output from a corresponding pupil tracking system, or a predicted pupil location, for example, when the process 1100 is implemented at a higher refresh rate than that otherwise available from the pupil tracking system, for instance. As will be appreciated by the skilled artisan, the input pupil location 1308 may be provided by an external pupil tracking engine and/or devices 1305, or again provided by an internal engine and/or integrated devices, depending the application and implementation at hand. For example, a self-contained digital display device such as a mobile phone, tablet, laptop computer, digital television, or the like may include integrated hardware to provide real time pupil tracking capabilities, such as an integrated camera and machine vision-based pupil tracking engine; integrated light source, camera and glint-based pupil tracking engine; and/or a combination thereof. In other embodiments or implementations, external pupil tracking hardware and/or firmware may be leveraged to provide a real time pupil location. For example, a vehicular dashboard, control or entertainment display may interface with an external camera(s) and/or pupil tracking hardware to produce a similar effect. Naturally, the integrated or distributed nature of the various hardware, firmware and/or software components required to execute the predictive pupil tracking functionalities described herein may vary for different applications, implementations and solution at hand.

The pupil location 1308, in one embodiment, is the three-dimensional coordinates of at least one the user's pupils' center with respect to a given reference frame, for example a point on the device or display. This pupil location 1308 may be derived from any eye/pupil tracking method known in the art. In some embodiments, the pupil location 1308 may be determined prior to any new iteration of the rendering algorithm, or in other cases, at a lower framerate. In some embodiments, only the pupil location of a single user's eye may be determined, for example the user's dominant eye (i.e. the one that is primarily relied upon by the user). In some embodiments, this position, and particularly the pupil distance to the screen may otherwise or additionally be rather approximated or adjusted based on other contextual or environmental parameters, such as an average or preset user distance to the screen (e.g. typical reading distance for a given user or group of users; stored, set or adjustable driver distance in a vehicular environment; etc.).

Figure 4A:
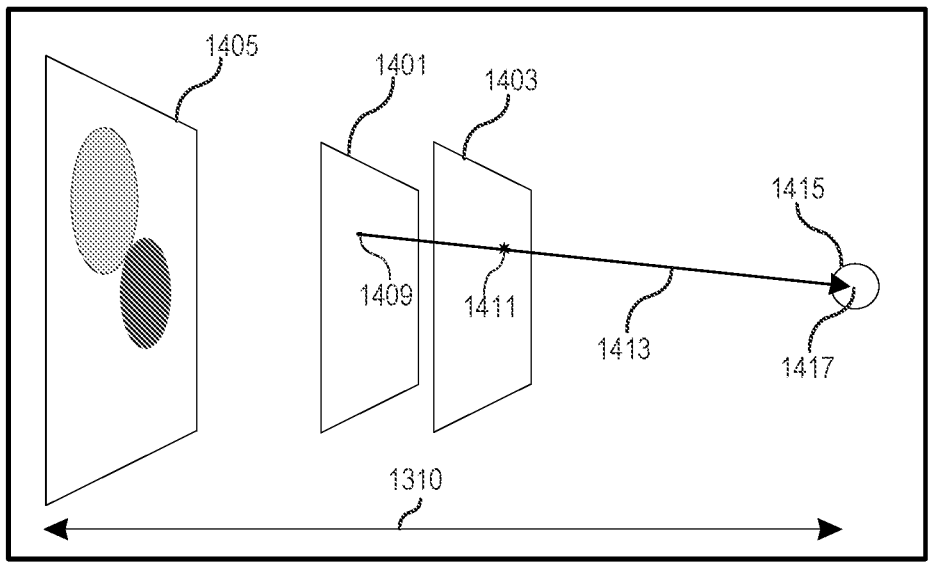
FIGS. 4A to 4C are schematic diagrams illustrating certain process steps of FIG. 2.
Figure 4B:
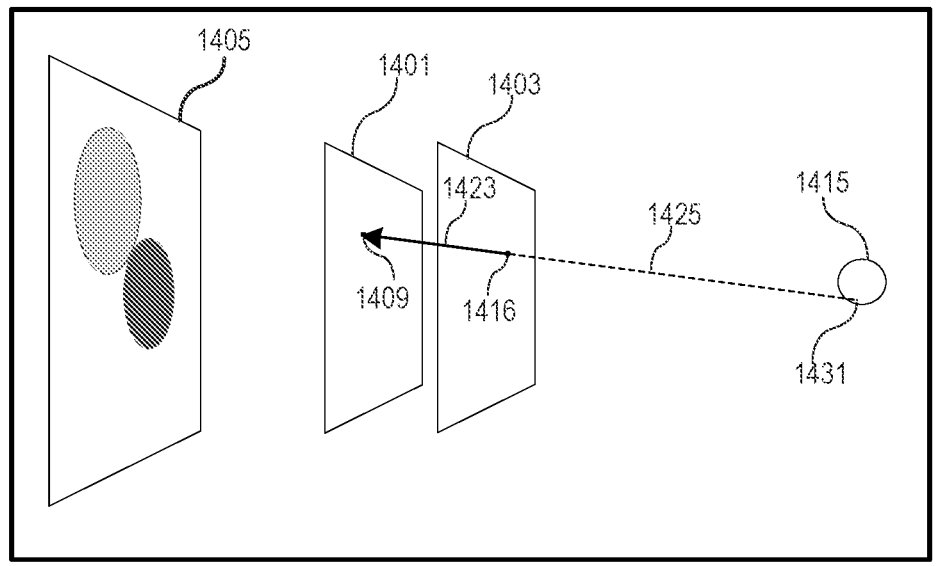
Figure 4C:
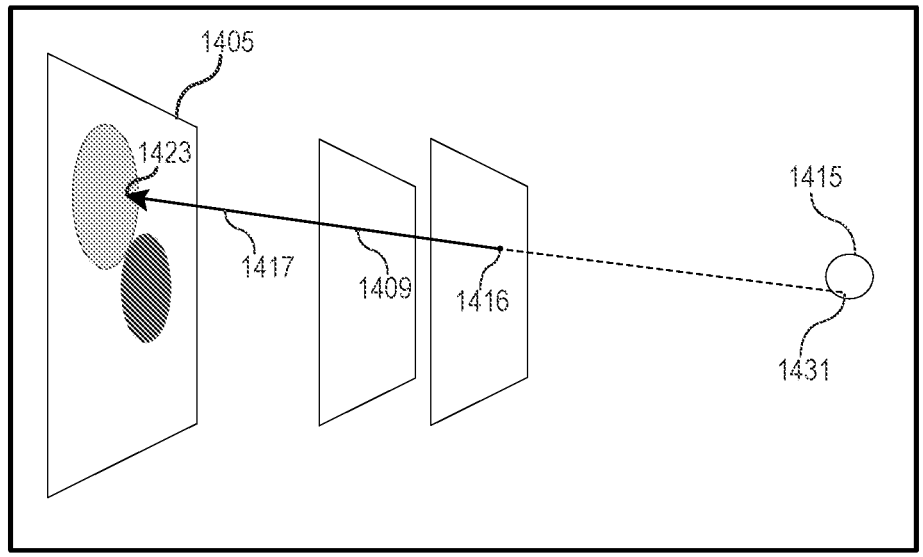

With added reference to FIGS. 4A to 4C, once constant parameters 1102, user parameters 1103, and variables 1104 have been set, the method of FIG. 2 then proceeds with step 1106, in which the minimum reading distance 1310 (and/or related parameters) is used to compute the position of a virtual (adjusted) image plane 1405 with respect to the device's display, followed by step 1108 wherein the size of image 1306 is scaled within the image plane 1405 to ensure that it correctly fills the pixel display 1401 when viewed by the distant user. This is illustrated in FIG. 4A, which shows a diagram of the relative positioning of the user's pupil 1415, the light field shaping layer 1403, the pixel display 1401 and the virtual image plane 1405. In this example, the size of image 1306 in image plane 1405 is increased to avoid having the image as perceived by the user appear smaller than the display's size.

Figure 6:
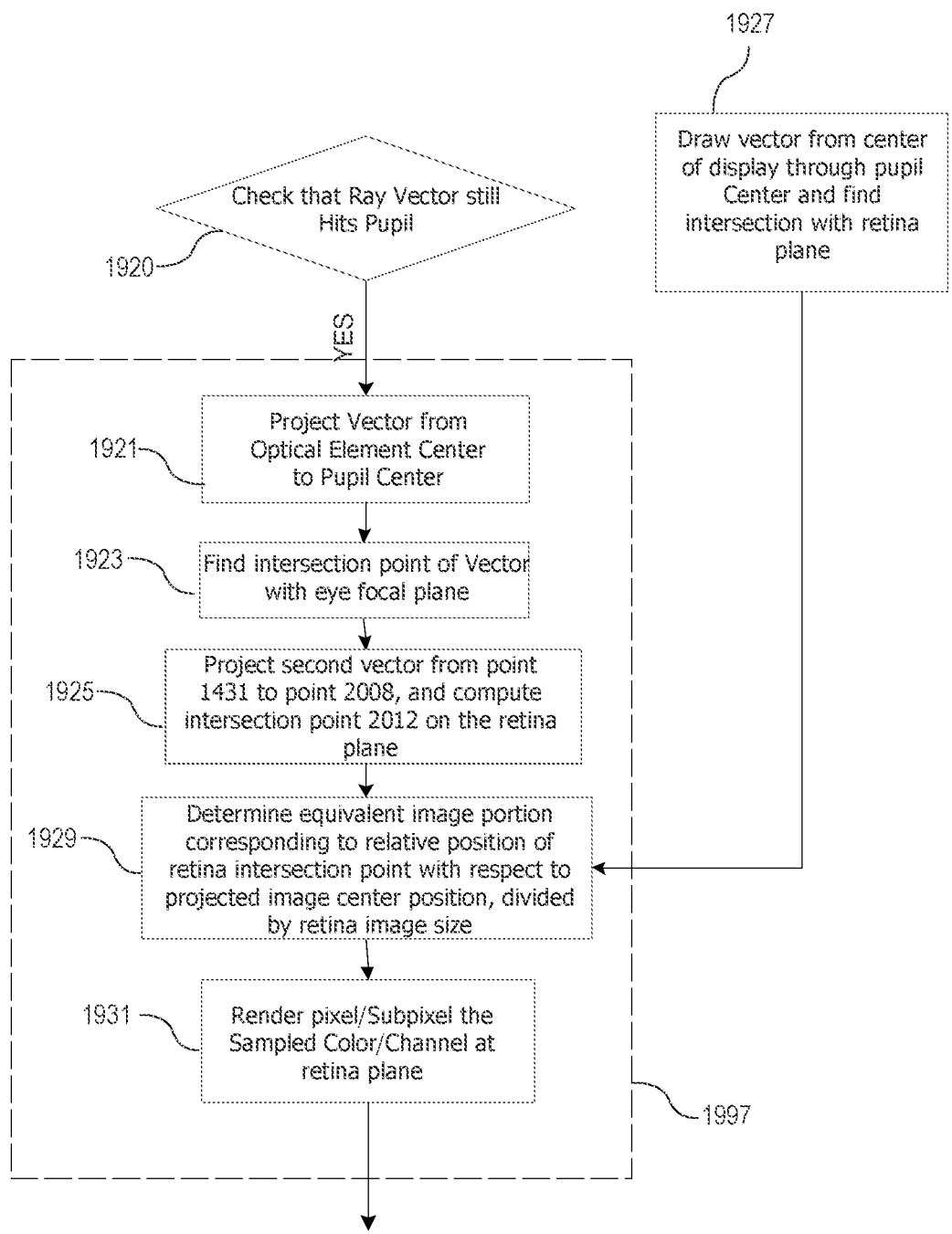
FIG. 6 is a process flow diagram of step 1997 of the process of FIG. 5, in accordance with one embodiment.

An exemplary ray-tracing methodology is described in steps 1109 to 1128 of FIG. 2, at the end of which the output color of each pixel of pixel display 1401 is known so as to virtually reproduce the light field emanating from an image 1306 positioned at the virtual image plane 1405. In FIG. 6, these steps are illustrated in a loop over each pixel in pixel display 1401, so that each of steps 1109 to 1126 describes the computations done for each individual pixel. However, in some embodiments, these computations need not be executed sequentially, but rather, steps 1109 to 1128 may executed in parallel for each pixel or a subset of pixels at the same time. Indeed, as will be discussed below, this exemplary method is well suited to vectorization and implementation on highly parallel processing architectures such as GPUs. Moreover, note that the loop from steps 1909 to 1934 can be done on all pixels or on a subset of selected pixels only, as was described above.

As illustrated in FIG. 4A, once a new pixel for which ray-tracing is to be done is chosen at step 1909, in step 1110, for a given pixel 1409 in pixel display 1401, a trial vector 1413 is first generated from the pixel's position to the (actual or predicted) center position 1417 of pupil 1415. This is followed in step 1112 by calculating the intersection point 1411 of vector 1413 with the LFSL 1403.

The method then finds, in step 1114, the coordinates of the center 1416 of the LFSL optical element closest to intersection point 1411. Once the position of the center 1416 of the optical element is known, in step 1116, a normalized unit ray vector is generated from drawing and normalizing a vector 1423 drawn from center position 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. The direction of this ray vector will be used to find the portion of image 1306, and thus the associated color, represented by pixel 1409. But first, in step 1118, this ray vector is projected backwards to the plane of pupil 1415, and then in step 1120, the method verifies that the projected ray vector 1425 is still within pupil 1415 (i.e. that the user can still "see" it). Once the intersection position, for example location 1431 in FIG. 4B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

If this deviation is deemed to be too large (i.e. light emanating from pixel 1409 channeled through optical element 1416 is not perceived by pupil 1415), then in step 1122, the method flags pixel 1409 as unnecessary and to simply be turned off or render a black color. Otherwise, as shown in FIG. 14C, in step 1124, the ray vector is projected once more towards virtual image plane 1405 to find the position of the intersection point 1423 on image 1306. Then in step 1126, pixel 1409 is flagged as having the color value associated with the portion of image 1306 at intersection point 1423.

In some embodiments, method 1100 is modified so that at step 1120, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1220 continues to step 1124. At step 1126, the pixel color value assigned to pixel 1409 is chosen to be somewhere between the full color value of the portion of image 1306 at intersection point 1423 or black, depending on the value of the interpolation function used at step 1120 (1 or 0).

In yet other embodiments, pixels found to illuminate a designated area around the pupil may still be rendered, for example, to produce a buffer zone to accommodate small movements in pupil location, for example, or again, to address potential inaccuracies, misalignments or to create a better user experience.

In some embodiments, steps 1118, 1120 and 1122 may be avoided completely, the method instead going directly from step 1116 to step 1124. In such an exemplary embodiment, no check is made that the ray vector hits the pupil or not, but instead the method assumes that it always does.

Once the output colors of all pixels have been determined, these are finally rendered in step 1130 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

With reference to FIGS. 5, 6 and 7A to 7D, and in accordance with one embodiment, another exemplary computationally implemented ray-tracing method for rendering an adjusted image via the light field shaping layer (LFSL) that accommodates for the user's reduced visual acuity, for example, will now be described. In this embodiment, the adjusted image portion associated with a given pixel/sub-pixel is computed (mapped) on the retina plane instead of the virtual image plane considered in the above example, again in order to provide the user with a designated image perception adjustment. Therefore, the currently discussed exemplary embodiment shares some steps with the method of FIG. 2. Indeed, a set of constant parameters 502 may also be pre-determined. These may include, for example, any data that are generally based on the physical and functional characteristics of the display for which the method is to be implemented, as will be explained below. Similarly, user parameters 503 may also be determined which, for example, are not expected to significantly change during a user's viewing session, for instance. Finally, every iteration of the rendering algorithm may use a set of input variables 504 which are expected to change either at each rendering iteration or at least between each user viewing session. The list of possible variables and constants is substantially the same as the one disclosed in FIG. 3 and will thus not be replicated here.

Once constant parameters 502, user parameters 503, and variables 504 have been set, this second exemplary ray-tracing methodology proceeds from steps 1909 to 1936, at the end of which the output color of each pixel of the pixel display is known so as to virtually reproduce the light field emanating from an image perceived to be positioned at the correct or adjusted image distance, in one example, so to allow the user to properly focus on this adjusted image (i.e. having a focused image projected on the user's retina) despite a quantified visual aberration. In FIG. 5, these steps are illustrated in a loop over each pixel in pixel display 1401, so that each of steps 1909 to 1934 describes the computations done for each individual pixel. However, in some embodiments, these computations need not be executed sequentially, but rather, steps 1909 to 1934 may be executed in parallel for each pixel or a subset of pixels at the same time. Indeed, as will be discussed below, this second exemplary method is also well suited to vectorization and implementation on highly parallel processing architectures such as GPUs. Moreover, note that the loop from steps 1909 to 1934 can be done on all pixels or on a subset of selected pixels only, as was described above.

Figure 7A:
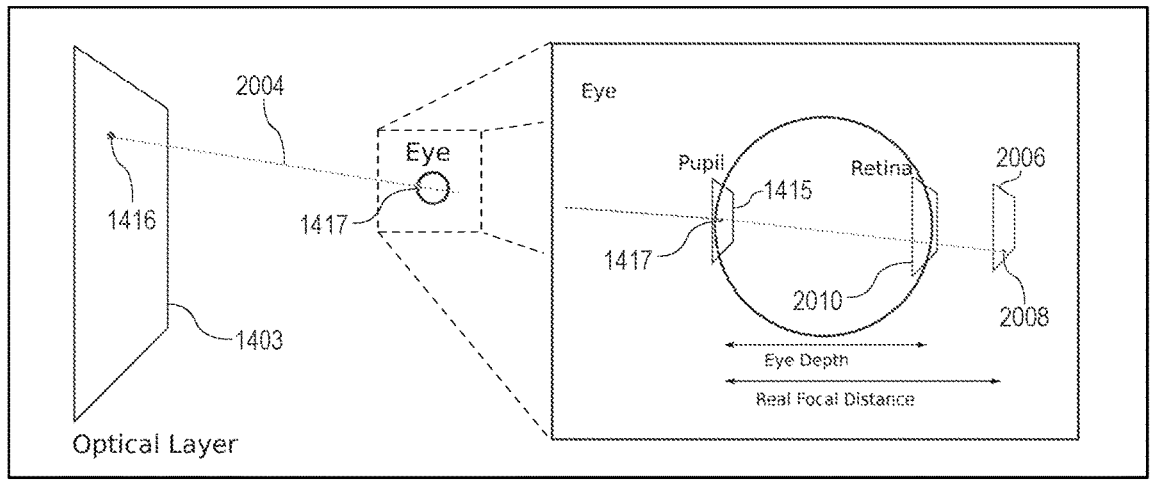
FIGS. 7A to 7D are schematic diagrams illustrating certain process steps of FIGS. 5 and 6.
Figure 7B:
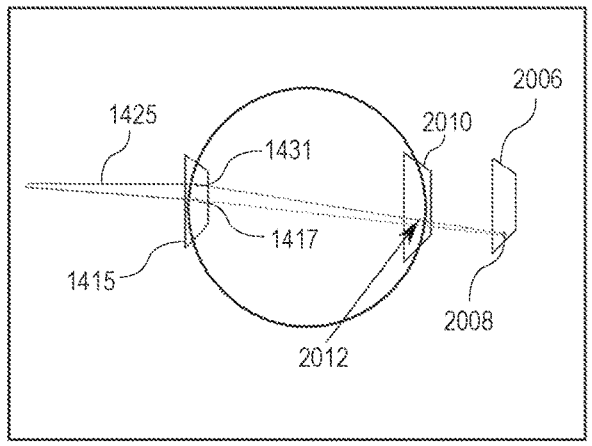
Figure 7C:
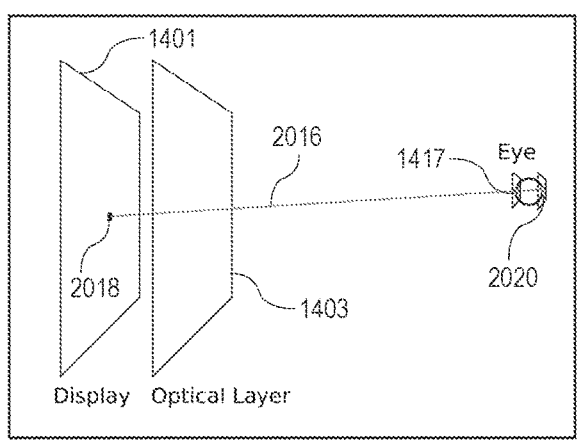
Figure 7D:
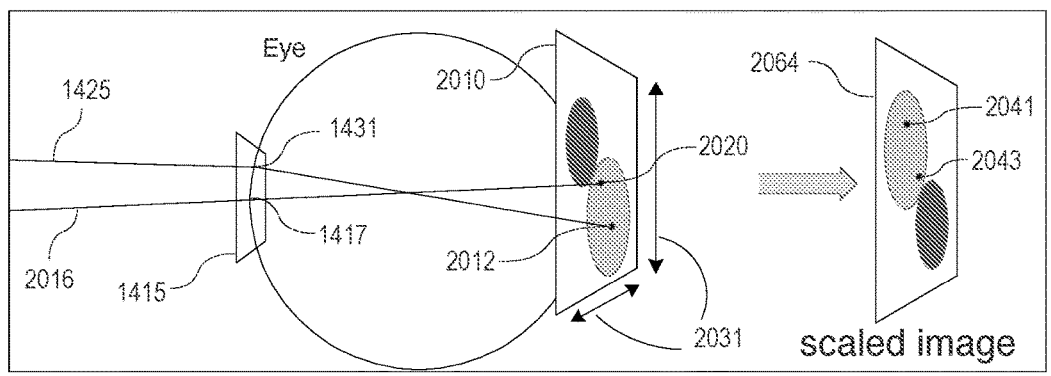

Referencing once more FIG. 7A, once a new pixel for which ray-tracing is to be done is chosen at step 1909, in step 1910 (as in step 1110), for a given pixel in pixel display 1401, a trial vector 1413 is first generated from the pixel's position to (actual or predicted) pupil center 1417 of the user's pupil 1415. This is followed in step 1912 by calculating the intersection point of vector 1413 with optical layer 1403.

From there, in step 1914, the coordinates of the optical element center 1416 closest to intersection point 1411 are determined. This step may be computationally intensive and will be discussed in more depth below. As shown in FIG. 9B, once the position of the optical element center 1416 is known, in step 1916, a normalized unit ray vector is generated from drawing and normalizing a vector 1423 drawn from optical element center 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. In step 1918, this ray vector is projected backwards to pupil 1415, and then in step 1920, the method ensures that the projected ray vector 1425 is still within pupil 1415 (i.e. that the user can still "see" it). Once the intersection position, for example location 1431 in FIG. 14B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

Now referring to FIGS. 6 and 11A to 11D, steps 1921 to 1929 of method 1900 will be described. Once optical element center 1416 of the relevant optical unit has been determined, at step 1921, a vector 2004 is drawn from optical element center 1416 to (actual or predicted) pupil center 1417. Then, in step 1923, vector 2004 is projected further behind the pupil plane onto eye focal plane 2006 (location where any light rays originating from optical layer 1403 would be focused by the eye) to locate focal point 2008. For a user with perfect vision, focal plane 2006 would be located at the same location as retina plane 2010, but in this example, focal plane 2006 is located behind retina plane 2010, which would be expected for a user with some form of farsightedness. The position of focal plane 2006 may be derived from the user's minimum reading distance 1310, for example, by deriving therefrom the focal length of the user's eye. Other manually input or computationally or dynamically adjustable means may also or alternatively be consider to quantify this parameter.

The skilled artisan will note that any light ray originating from optical element center 1416, no matter its orientation, will also be focused onto focal point 2008, to a first approximation. Therefore, the location 2012 on retina plane 2010 onto which light entering the pupil at intersection point 1431 will converge may be approximated by drawing a straight line between intersection point 1431 where ray vector 1425 hits the pupil 1415 and focal point 2008 on focal plane 2006. The intersection of this line with retina plane 2010 (retina image point 2012) is thus the location on the user's retina corresponding to the image portion that will be reproduced by corresponding pixel 1409 as perceived by the user. Therefore, by comparing the relative position of retina point 2012 with the overall position of the projected image on the retina plane 2010, the relevant adjusted image portion associated with pixel 1409 may be computed.

To do so, at step 1927, the corresponding projected image center position on retina plane 2010 is calculated. Vector 2016 is generated originating from the center position of display 1401 (display center position 2018) and passing through pupil center 1417. Vector 2016 is projected beyond the pupil plane onto retina plane 2010, wherein the associated intersection point gives the location of the corresponding retina image center 2020 on retina plane 2010. The skilled technician will understand that step 1927 could be performed at any moment prior to step 1929, once the relative pupil center location 1417 is known in input variables step 1904. Once image center 2020 is known, one can then find the corresponding image portion of the selected pixel/subpixel at step 1929 by calculating the x/y coordinates of retina image point 2012 relative to retina image center 2020 on the retina, scaled to the x/y retina image size 2031.

This retina image size 2031 may be computed by calculating the magnification of an individual pixel on retina plane 2010, for example, which may be approximately equal to the x or y dimension of an individual pixel multiplied by the eye depth 1314 and divided by the absolute value of the distance to the eye (i.e. the magnification of pixel image size from the eye lens). Similarly, for comparison purposes, the input image is also scaled by the image x/y dimensions to produce a corresponding scaled input image 2064. Both the scaled input image and scaled retina image should have a width and height between −0.5 to 0.5 units, enabling a direct comparison between a point on the scaled retina image 2010 and the corresponding scaled input image 2064, as shown in FIG. 20D.

From there, the image portion position 2041 relative to retina image center position 2043 in the scaled coordinates (scaled input image 2064) corresponds to the inverse (because the image on the retina is inverted) scaled coordinates of retina image point 2012 with respect to retina image center 2020. The associated color with image portion position 2041 is therefrom extracted and associated with pixel 1409.

In some embodiments, method 1900 may be modified so that at step 1920, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1920 continues to step 1124. At step 1931, the pixel color value assigned to pixel 1409 is chosen to be somewhere between the full color value of the portion of image 1306 at intersection point 1423 or black, depending on the value of the interpolation function used at step 1920 (1 or 0).

In yet other embodiments, pixels found to illuminate a designated area around the pupil may still be rendered, for example, to produce a buffer zone to accommodate small movements in pupil location, for example, or again, to address potential inaccuracies or misalignments.

Now back to FIG. 5, once the output colors of all pixels in the display have been determined (check at step 1934 is true), these are finally rendered in step 1936 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

As will be appreciated by the skilled artisan, selection of the adjusted image plane onto which to map the input image in order to adjust a user perception of this input image allows for different ray tracing approaches to solving a similar challenge, that is of creating an adjusted image using the light field display that can provide an adjusted user perception, such as addressing a user's reduce visual acuity. While mapping the input image to a virtual image plane set at a designated minimum (or maximum) comfortable viewing distance can provide one solution, the alternate solution may allow accommodation of different or possibly more extreme visual aberrations. For example, where a virtual image is ideally pushed to infinity (or effectively so), computation of an infinite distance becomes problematic. However, by designating the adjusted image plane as the retinal plane, the illustrative process of FIG. 5 can accommodate the formation of a virtual image effectively set at infinity without invoking such computational challenges. Likewise, while first order focal length aberrations are illustratively described with reference to FIG. 5, higher order or other optical anomalies may be considered within the present context, whereby a desired retinal image is mapped out and traced while accounting for the user's optical aberration(s) so to compute adjusted pixel data to be rendered in producing that image. These and other such considerations should be readily apparent to the skilled artisan.

While the computations involved in the above described ray-tracing algorithms (steps 1110 to 1128 of FIG. 6 or steps 1920 to 1934 of FIGS. 5 and 6) may be done on general CPUs, it may be advantageous to use highly parallel programming schemes to speed up such computations. While in some embodiments, standard parallel programming libraries such as Message Passing Interface (MPI) or OPENMP may be used to accelerate the light field rendering via a general-purpose CPU, the light field computations described above are especially tailored to take advantage of graphical processing units (GPU), which are specifically tailored for massively parallel computations. Indeed, modern GPU chips are characterized by the very large number of processing cores, and an instruction set that is commonly optimized for graphics. In typical use, each core is dedicated to a small neighborhood of pixel values within an image, e.g., to perform processing that applies a visual effect, such as shading, fog, affine transformation, etc. GPUs are usually also optimized to accelerate exchange of image data between such processing cores and associated memory, such as RGB frame buffers. Furthermore, smartphones are increasingly being equipped with powerful GPUs to speed the rendering of complex screen displays, e.g., for gaming, video, and other image-intensive applications. Several programming frameworks and languages tailored for programming on GPUs include, but are not limited to, CUDA, OpenCL, OpenGL Shader Language (GLSL), High-Level Shader Language (HLSL) or similar. However, using GPUs efficiently may be challenging and thus require creative steps to leverage their capabilities, as will be discussed below.

Figure 8:
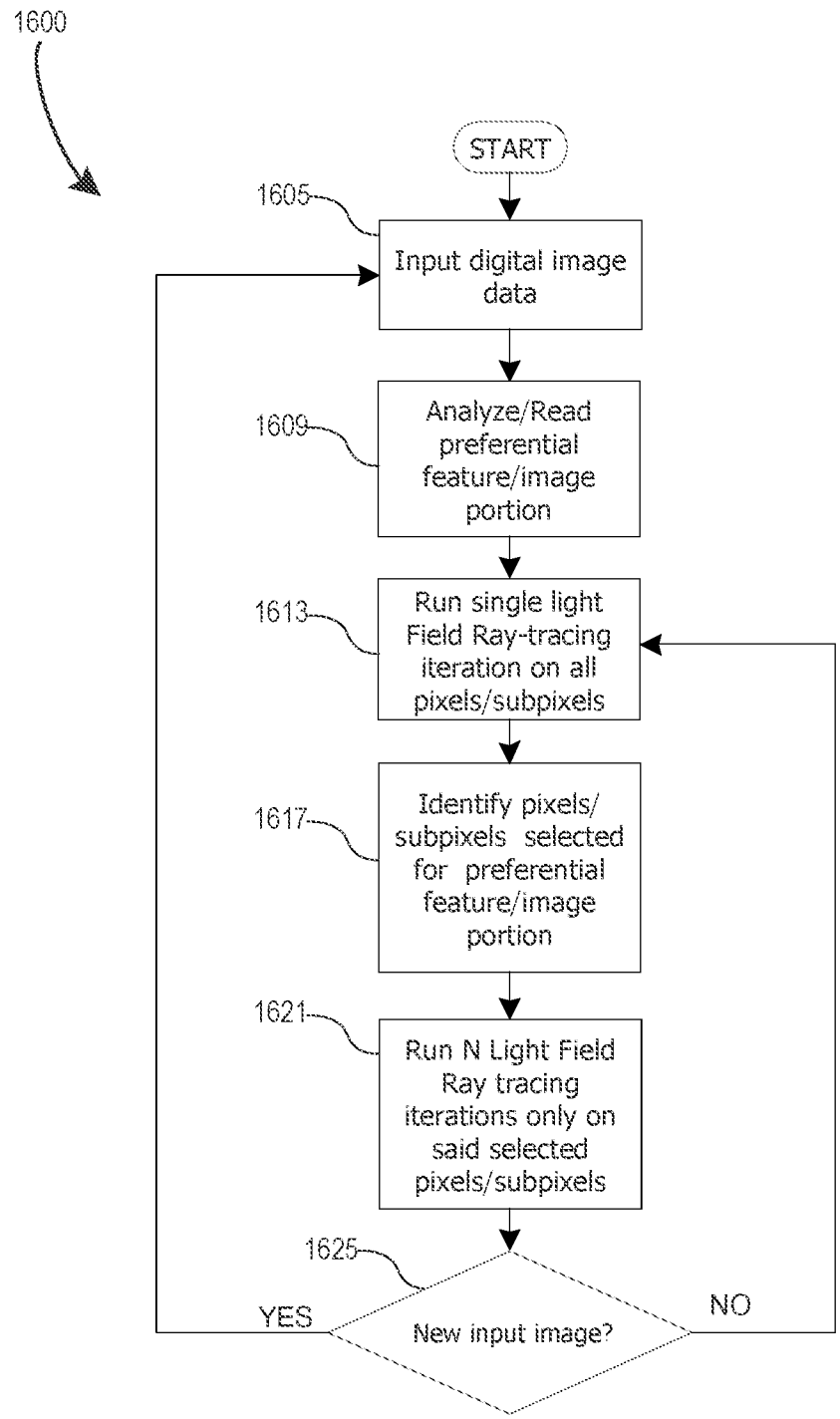
FIG. 8 is a process flow diagram of an illustrative selective light field rendering process, in accordance with one embodiment.

With reference to FIG. 8 and in accordance with one embodiment, a selective light field rendering method for rendering selected features and/or image portions within an input digital image via a light field display, generally referred to using the numeral 1600, will now be described. In the embodiment described herein, the system receives as input a digital image at step 1605 to be displayed selectively via the light field display. Selected features and/or image portions to be displayed via light field are identified at step 1609. In some embodiments, this may include analyzing the input image via a detection engine as explained above, while in other embodiments the information regarding the selected features and/or image portions may be already contained and/or encoded in the file format of the input digital image, for example by running the detection engine at a prior time or again for text-based portions natively encoding such text; in which case step 1609 would only read this information from the data file itself. Once all selected features/image portions are known, the process proceeds to step 1613, wherein a full iteration of the light field ray tracing algorithm is run once on every pixels/subpixels of the digital display. As explained above while discussing the ray-tracing algorithms of FIG. 2 and FIG. 5, this results in matching every pixel/subpixels of the digital display with an image location of the associated virtual image on a virtual image plane. This association between each pixel/subpixel and a corresponding image location on the virtual image plane is recorded at step 1617. From this, the system may identify which pixel/subpixel is associated with a virtual image location that comprises the selected features and/or image portions of step 1609. This process step as described herein assumes that some variables, for example the user pupil location, does not change noticeably (e.g. that the association between pixels/subpixels and selected image portion is still true). Some viewing environments that limit the range of motion of a user may be well suited for this, for example but not limited to a car dashboard or similar, or again within the context of a typically static e-reader environment where user motion is typically limited. Moreover, note that the association is valid even if the input image changes but the pupil location stays constant. In some embodiments, as illustrated, at step 1621 a partial light field ray-tracing loop on selected pixels/subpixels only may be done a number of times, for example N times where N is a constant equal to a value of one or more. The method checks at step 1625 if the image to be displayed as changed, in which case the whole process starts anew from step 1605. If not, the method goes back to step 1613 to run the ray-tracing algorithm on all pixels/subpixels once more to refresh the association between each pixel/subpixel and corresponding image portions of the input image. The ratio of partial/selected ray-tracing loops to complete ray-tracing loops depends on the type of viewing environment. For example, the less motion the user's pupil has, the larger value of N may be used.

Figure 9:
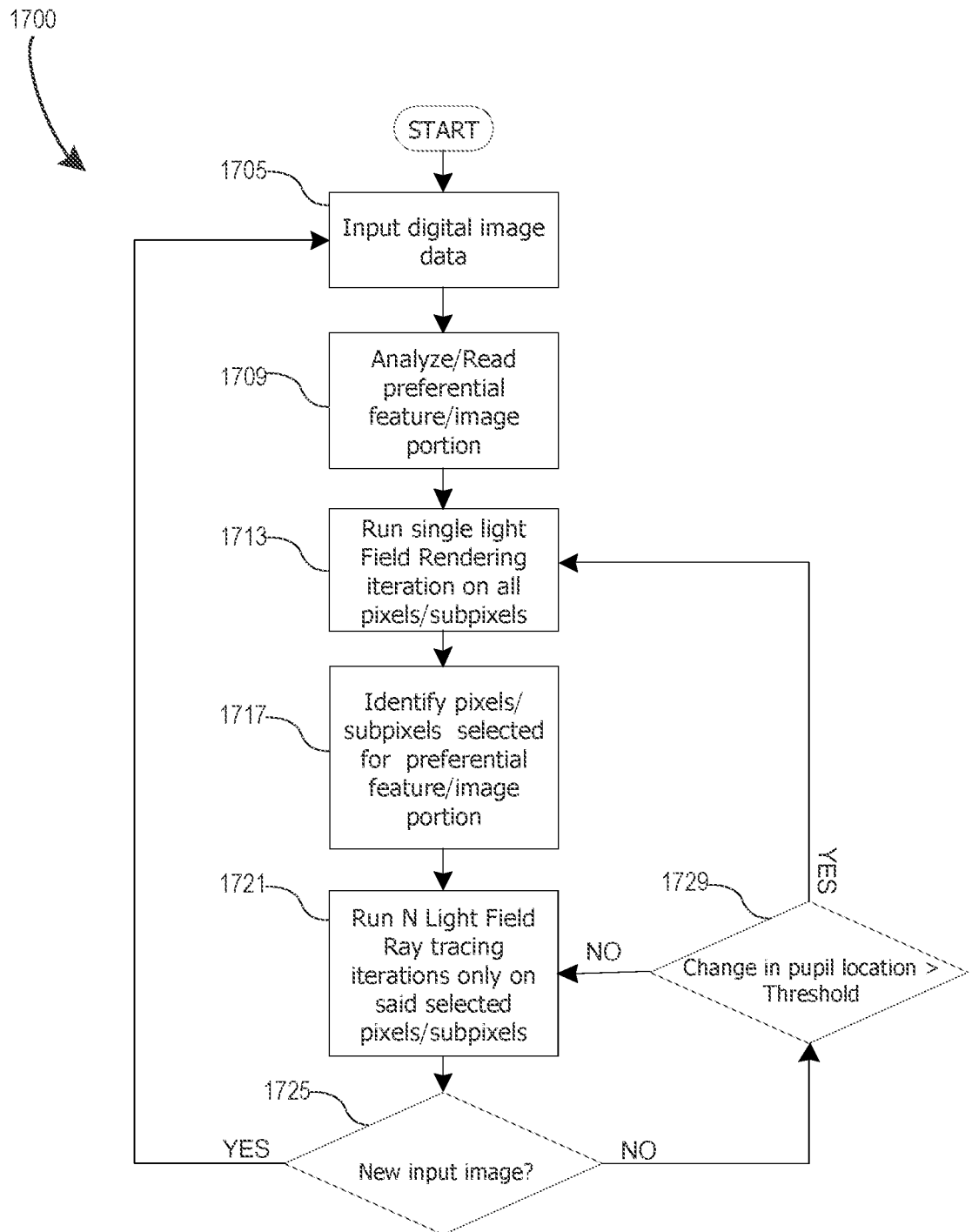
FIG. 9 is a process flow diagram of another illustrative selective light field rendering process, in accordance with one embodiment.

With reference to FIG. 9 and in accordance with one embodiment, another selective light field rendering method for rendering selected features and/or image portions within an input digital image via a light field display, generally referred to using the numeral 1700, will now be described. FIG. 9 shows a variation of the process illustrated in FIG. 8 wherein the process may herein dynamically determine the number of times the ray-tracing algorithm is run on the selected pixels/subpixels only. Steps 1705 to 1725 are more or less the same as steps 1605 to 1625 of FIG. 8 described above. However, here the location of the user's pupil is recorded at each ray-tracing iteration (e.g. steps 1713 and 1721). Therefore, the change in position of the current user's pupil location (last iteration of step 1721) with respect to the pupil location at the time of the last update on all pixels/subpixels (step 1713) may be used to determine (via a threshold displacement or similar) if a new iteration on all pixels/subpixels is warranted. This is done at step 1729. In the case where the calculated distance between the two pupil locations (step 1713 and last iteration of step 1721) is larger than a threshold value, then the process goes directly to step 1713 once more to refresh the association between each pixel/subpixel and the corresponding image portions of the input image, while in the opposite case the process continues a selective ray-tracing iteration of step 1721. The process then continues alternating between doing a ray-tracing iteration on all pixels/subpixels and one or more iterations only on selected pixels/subpixels, until the system is turned off or if a new image is inputted into the rendering pipeline at step 1725, in which case the process starts once more from the beginning (step 1705).

Figure 10:
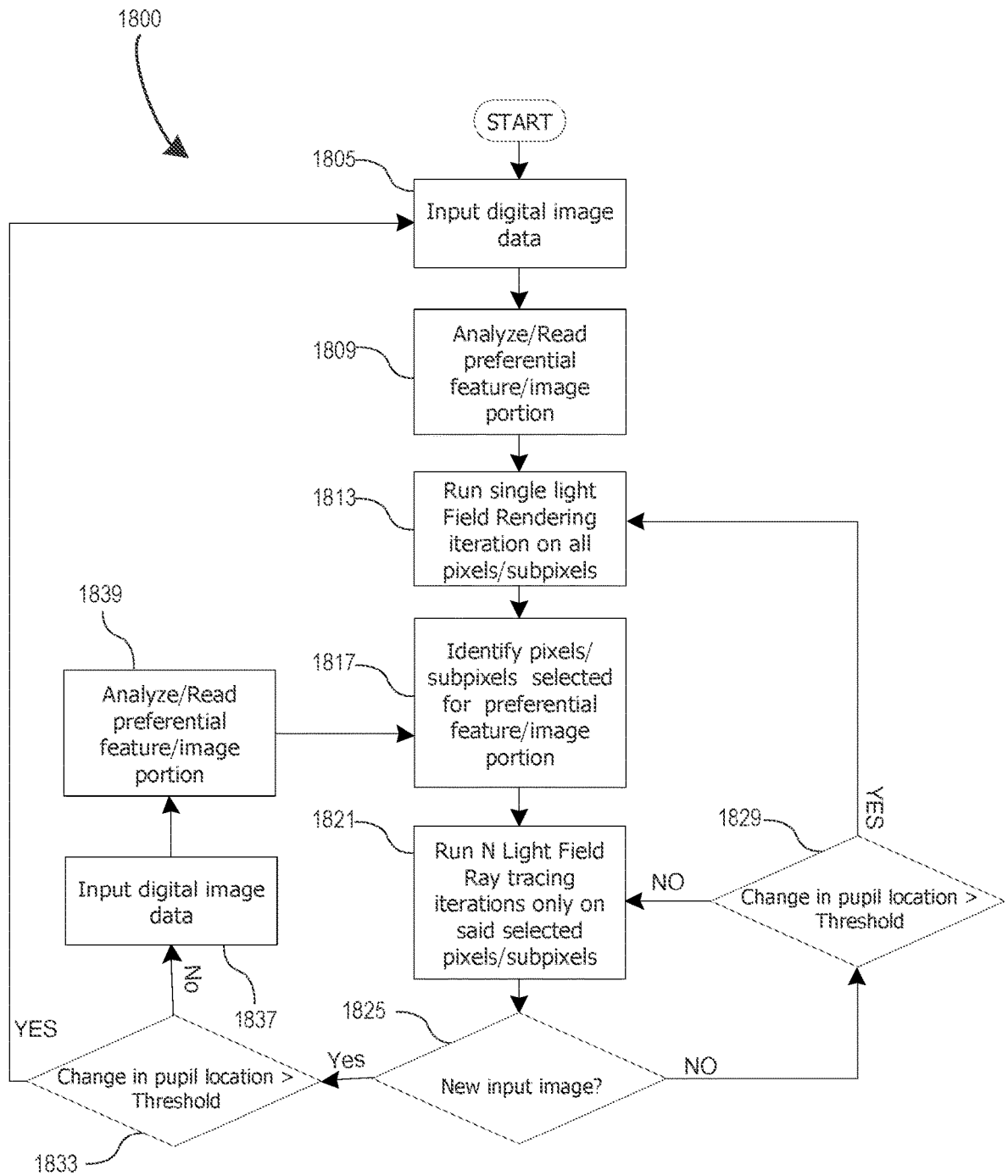
FIG. 10 is a process flow diagram of yet another illustrative selective light field rendering process, in accordance with one embodiment.

With reference to FIG. 10, and in accordance with one embodiment, another selective light field rendering method for rendering selected features and/or image portions within an input digital image via a light field display, generally referred to using the numeral 1800, will now be described. FIG. 10 shows a variation of the process described in FIG. 9, but wherein the process further checks, upon receiving a new input image and in the case where the user pupil hasn't moved at all or too little, skips the step of ray-tracing the image for all pixels/subpixels. This is possible because the association computed between each pixels/subpixels and a corresponding image location on the virtual image plane hasn't changed (significantly). Therefore, steps 1805 to 1829 are the same as corresponding steps 1705 to 1729 of FIG. 9. However, the method further comprises the additional step of, once a new input image is detected at step 1825, calculating the user's pupil displacement with respect to the pupil location at the last iteration of step 1813 (similar to step 1829). If the pupil location hasn't moved too far away (e.g. within a threshold distance), then the method proceeds with steps 1837 and 1839, which are substantially identical to steps 1805 and 1809 (e.g. reading the new input image and analyzing/reading therein the selected image portions and/or features). The method can then move directly to step 1817 to render selectively the image portions and/or features (effectively skipping the step of ray-tracing on all pixels/subpixels of step 1815). As mentioned above, this may be done because the association between each pixel/subpixel and a given image location on the virtual image plane only changes if the pupil location changes. Therefore, the same association may be reused with the new input image to identify the pixels/subpixels corresponding to the new image portion and/or features. However, if the user's pupil has moved too much, then the method goes back to steps 1805, 1809 and 1813 where a full iteration of the ray-tracing algorithm is run on all pixels/subpixels to re-calculated the association between each pixel/subpixel and each corresponding image location on the virtual image plane.

As detailed above, various ray-tracing implementations may be invoked, to different degrees and based on different usage scenarios, to produce geometrically accurate vision corrected, or like perception adjusted outputs, based, at least in part, as a function of a tracked pupil location. As noted above, however, some embodiments may also or alternatively at least partially rely on stored vision corrected font patterns to produce similar effects particularly, for example, where limited pupil location tracking may be required (e.g. substantially static viewing environments), where a user may naturally adjust their position and/or where the user's vision may naturally accommodate for minor geometric variations so to bypass the need for pupil tracking entirely (or at least by-pass ongoing or full fledged pupil tracking and/or ray tracing processes). These and other such implementations are intended to fall within the general scope and context of the present disclosure.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A digital display device to render an image for viewing by a viewer having reduced visual acuity, the device comprising:
    a digital display medium for rendering the image based on pixel data related thereto;
    a complementary light field display portion; and
    a hardware processor operable on said pixel data for a selected portion of the image to be rendered via said complementary light field display portion so to produce vision-corrected pixel data corresponding thereto to at least partially address the viewer's reduced visual acuity when viewing said selected portion as rendered in accordance with said vision-corrected pixel data by said complementary light field display portion.

2. The digital display device of claim 1, wherein said complementary light field display portion comprises a distinctly operated light field display medium that is mechanically segregated from said digital display medium within a common digital display device housing.

3. The digital display device of claim 1, wherein said complementary light field display portion comprises a distinctly operated light field display medium that is detachably coupled to said digital display medium.

4. The digital display device of claim 1, wherein said complementary light field display portion comprises a distinctly operated light field display medium that is pivotably coupled relative to said digital display medium so to selectively form an angle relative thereto.

5. The digital display device of claim 1, wherein said complementary light field display portion comprises a distinctly addressable portion of said digital display medium.

6. The digital display device of claim 1, wherein the device comprises a touch sensitive graphical user interface rendered by said digital display medium, and wherein said selected portion is selected in response to a selective viewer input received via said touch sensitive graphical user interface.

7. The digital display device of claim 1, wherein the device comprises an external user interface external to said digital display medium, and wherein said selected portion is selected in response to a selective viewer input received via said external interface.

8. The digital display device of claim 1, wherein the image comprises text, and wherein said vision-corrected portion comprises vision-corrected text that is restricted to vision-corrected font portions.

9. The digital display device of claim 8, wherein said hardware processor is operable on pixel data to output corrective font pixel data to be rendered via said complementary light field display, wherein said corrective font pixel data for distinct text characters in the text corresponds to distinct corrective light field font pixel patterns that, when viewed via said light field display, render distinct vision corrected text characters accordingly.

10. The digital display device of claim 9, wherein each of said distinct corrective light field font pixel patterns in the text is stored and retrieved from a digital corrective font pattern library.

11. The digital display device of claim 10, wherein said distinct corrective light field font pixel patterns are stored as a function of a corrective power defined at least in part by the viewer's reduced visual acuity.

12. The digital display device of claim 1, wherein the digital display device comprises one of a mobile phone, a smartphone, a tablet, or an e-reader.

13. The digital display device of claim 1, wherein said selective viewer input is associated with a digital pointer selectively operable by the viewer to select said portion, wherein said portion is defined by an area on said digital display medium corresponding with a digital pointer location on said digital display medium.

14. The digital display device of claim 1, wherein said hardware processor is further operable to:
    identify a text area to be correctively rendered;
    define corrective font pixel data to be rendered via said light field display so to produce vision-corrected text; and
    render the corrective font pixel data so to produce said vision-corrected text to at least partially address the viewer's reduced visual acuity.

15. The digital display device of claim 14, wherein said defining comprises defining said corrective font pixel data for distinct text characters in the text to correspond to distinct corrective light field font pixel patterns that, when projected through said light field display, render distinct vision corrected text characters accordingly.

16. The digital display device of claim 14, wherein said identifying comprises automatically recognizing said distinct text characters, and wherein said defining comprises retrieving from digital storage said distinct corrective light field font pixel patterns corresponding to said automatically recognized text characters.

17. The digital display device of claim 14, wherein said defining comprises executing a digitally implemented ray-tracing process to:
- digitally map the text on an adjusted image plane designated to at least partially address the viewer's reduced visual acuity; and
- associate said corrective font pixel data with corresponding pixels according to said mapping and a physical geometry of the display medium and the viewer.

18. The digital display device of claim 17, wherein said adjusted image plane is a virtual image plane virtually positioned relative to the digital display at a designated distance from the viewer, wherein said designated distance comprises a minimum viewing distance designated a function of the viewer's reduced visual acuity.

19. The digital display device of claim 17, wherein said adjusted image plane is designated as a user retinal plane.

20. The digital display device of any one of claim 1, wherein said complementary light field display comprises a pixelated image rendering medium and an array of light field shaping elements disposed relative thereto, wherein said light field shaping elements form at least one of a microlens array or a parallax barrier.

* * * * *

UNITED STATES PATENT AND TRADEMARK OFFICE
CERTIFICATE OF CORRECTION

PATENT NO. : 11,635,617 B2
APPLICATION NO. : 17/594662
DATED : April 25, 2023
INVENTOR(S) : Raul Mihali et al.

It is certified that error appears in the above-identified patent and that said Letters Patent is hereby corrected as shown below:

On the Title Page

On Page 3, Column 1, Line 9, Item (56) under Other Publications, delete "at" and insert --et--.

In the Specification

In Column 1, Line 10, before "the" insert --is--.

In Column 2, Line 15, delete "(SiGGRAPH" and insert --(SIGGRAPH--.

In Column 2, Line 47, delete "Holographika" and insert --Holografika--.

In the Claims

In Column 31, Claim 20, Line 24, delete "of any one of" and insert --of--.

Signed and Sealed this
Eighth Day of August, 2023

Katherine Kelly Vidal
*Director of the United States Patent and Trademark Office*